US007803611B2

(12) United States Patent
Roelvink et al.

(10) Patent No.: US 7,803,611 B2
(45) Date of Patent: Sep. 28, 2010

(54) RNAI EXPRESSION CONSTRUCTS

(75) Inventors: Petrus W. Roelvink, Campbell, CA (US); David A. Suhy, Castro Valley, CA (US); Alexander A. Kolykhalov, Saratoga, CA (US); Linda Couto, Pleasanton, CA (US)

(73) Assignee: Benitec, Inc., Melbourne, Victoria (AU)

( * ) Notice: Subject to any disclaimer, the term of this patent is extended or adjusted under 35 U.S.C. 154(b) by 925 days.

(21) Appl. No.: 11/347,028

(22) Filed: Feb. 3, 2006

(65) Prior Publication Data

US 2007/0025969 A1 Feb. 1, 2007

Related U.S. Application Data

(60) Provisional application No. 60/649,641, filed on Feb. 3, 2005, provisional application No. 60/653,580, filed on Feb. 15, 2005.

(51) Int. Cl.
*C12N 15/00* (2006.01)
*C07H 21/04* (2006.01)
*A61K 31/70* (2006.01)

(52) U.S. Cl. .................. 435/320.1; 536/23.1; 536/24.5; 514/44

(58) Field of Classification Search ....................... None
See application file for complete search history.

(56) References Cited

U.S. PATENT DOCUMENTS

| | | | | |
|---|---|---|---|---|
| 6,218,181 | B1 | 4/2001 | Verma et al. | |
| 6,509,323 | B1 | 1/2003 | Davis et al. | |
| 6,573,099 | B2 | 6/2003 | Graham | |
| 2002/0162126 | A1 | 10/2002 | Beach et al. | |
| 2004/0053876 | A1 | 3/2004 | Turner et al. | |
| 2004/0214329 | A1 | 10/2004 | Kay et al. | |
| 2004/0220130 | A1* | 11/2004 | Robbins et al. | 514/44 |
| 2005/0008617 | A1* | 1/2005 | Chen et al. | 424/93.2 |
| 2005/0197313 | A1* | 9/2005 | Roelvink et al. | 514/44 |
| 2006/0128617 | A1* | 6/2006 | Kohara et al. | 514/12 |

FOREIGN PATENT DOCUMENTS

| | | |
|---|---|---|
| WO | WO 03/022052 A1 | 3/2003 |
| WO | WO 03/070750 | 8/2003 |
| WO | WO-03/070750 A | 8/2003 |
| WO | WO 03/078629 | 9/2003 |
| WO | WO-03/078629 A | 9/2003 |
| WO | WO 2004/011647 | 2/2004 |
| WO | WO-2004/011647 A | 2/2004 |
| WO | WO 2004/106517 | 12/2004 |
| WO | WO-2004/106517 A | 12/2004 |
| WO | WO 2005/087926 | 9/2005 |
| WO | WO-2005/087926 A | 9/2005 |

OTHER PUBLICATIONS

Wilson et al. PNAS 2003, vol. 100, pp. 2783-2788.*
Yonaha et al. EMBO Journal 2000, vol. 19, pp. 3770-3777.*
Partial International Search Report, mailed Jul. 13, 2006, for PCT No. PCT/US2006/004003.
Harborth et al., "Sequence, Chemical, and Structural Variation of Small Interfering RNAs and Short Hairpin RNAs and the Effect on Mammalian Gene Silencing," *Antisense and Nucleic Acid Drug Development*, 2003, vol. 13, No. 2, pp. 83-105.
Higashibata et al., "Identification of Promoter Regions Involved in Cell- and Developmental Stage-Specific Osteopontin Expression in Bone, Kidney, Placenta, and Mammary Gland: An Analysis of Transgenic Mice," *Journal of Bone and Mineral Research*, 2004, vol. 19, No. 1, pp. 78-88.
Grimm et al., "Liver Transduction with Recombinant Adeno-Associated Virus is Primarily Restricted by Capsid Serotype Not Vector Genotype," *Journal of Virology*, 2006, vol. 80, No. 1, pp. 426-439.
Grimm et al., "Preclinical In Vivo Evaluation of Pseudotyped Adeno-Associated Virus Vectors for Liver Gene Therapy," *Blood*, 2003, vol. 102, No. 7, pp. 2412-2419.
Furth et al., "Gene Transfer into Somatic Tissues by Jet Injection," *Analytical Biochemistry*, 1992, vol. 205, pp. 365-368.
De et al., "High Levels of Persistent Expression of α1-Antitrypsin Mediated by the Nonhuman Primate Serotype rh.10 Adeno-Associated Virus Despite Preexisting Immunity to Common Human Adeno-Associated Viruses," *Molecular Therapy*, 2006, vol. 13, No. 1, pp. 67-76.
Chen et al., "Minicircle DNA Vectors Devoid of Bacterial DNA Result in Persistent and High-Level Transgene Expression In Vivo," *Molecular Therapy*, 2003, vol. 8, No. 3, pp. 495-500.
Karlin et al., "Applications and Statistics for Multiple High-Scoring Segments in Molecular Sequences", *Proceedings of the National Academy of Science*, 1993, vol. 90, pp. 5873-5877.
Myers et al., "Optimal Alignments in Linear Space," *Computer Applications in the Biosciences*, 1988, vol. 4, No. 1, pp. 11-17.
Nakai et al., "Unrestricted Hepatocyte Transduction with Adeno-Associated Virus Serotype 8 Vectors in Mice," *Journal of Virology*, 2005, vol. 79, No. 1, pp. 214-224.
Pearson et al., "Improved Tools for Biological Sequence Comparison," *Proceedings of the National Academy of Science*, 1988, vol. 85, pp. 2444-2448.
Tang et al., "Genetic Immunization is a Simple Method for Eliciting an Immune Response," *Nature*, 1992, vol. 356, pp. 152-154.
Thomas et al., "Rapid Uncoating of Vector Genomes is the Key to Efficient Liver Transduction with Pseudotyped Adeno-Associated Virus Vectors," *Journal of Virology*, 2004, vol. 78, No. 6, pp. 3110-3122.
Zhu et al., "Sustained Whole-Body Functional Rescue in Congestive Heart Failure and Muscular Dystrophy Hamsters by Systemic Gene Transfer," *Circulation*, 2005, vol. 112, pp. 2650-2659.
Wang et al., "Rapid and Highly Effective Transduction By Double-Stranded Adeno-Associated Virus Vectors In Vitro and In Vivo," *Gene Therapy*, 2003, vol. 10, pp. 2105-2111.
D. Boden, et al., "Human Immunodeficiency Virus Type 1 Escape from RNA Interference", *Journal of Virology*, vol. 77, No. 21, Nov. 2003, pp. 11531-11535.

(Continued)

*Primary Examiner*—Tracy Vivlemore
(74) *Attorney, Agent, or Firm*—Patton Boggs LLP

(57) ABSTRACT

The present invention provides compositions and methods suitable for expressing 1-x RNAi agents against a gene or genes in cells, tissues or organs of interest in vitro and in vivo so as to treat diseases or disorders.

19 Claims, 10 Drawing Sheets

OTHER PUBLICATIONS

International Search Report for Application No. PCT/US2006/004003, mailed Dec. 20, 2006.
Fire et al., Nature, 391:806-11 (1998).
Tuschl et al., Genes and Dev., 13:3191-97 (1999).
Elbashir et al., Nature, 411:494-498 (2001).
Kurreck Eur. J. Biochem., 270:1628-44 (2003).
Boden et al., J. Virol., 77(21): 11531-11535 (2003).
Hoggatt et al., Circ. Res., Dec. 91(12):1151-59 (2002).
Sohal et al., Circ. Res., Jul. 89(1):20-25 (2001).
Zhang et al., Genome Res., Jan. 14(1):79-89 (2004).
Maraia et al., Nucleic Acids Res, 22(15):3045-52 (1994).
Maraia et al., Nucleic Acids Res., 24(18): 3552-59 (1996).
Xia et al., Nucleic Acids Res., 31(17): e100 (2003).
Gitlin et al., J. of Virol., 79: 1027-1035, (2005).
Nakai et al., J. Virol., 76:11343-349 (2002).
Kay et al., Nature, 424:251 (2003).
Thomas et al., Nature Reviews, Genetics, 4:346-58 (2003).
Tomar et al., Oncogene, 22:5712-15 (2003).
Mingozzi et al., J. Virol., 76(20): 10497-502 (2002).
Yant et al., Nature Biotech., 20:999-1004 (2002).
Perri et al., J. Virol., 74(20): 9802-07 (2002).
Yokota et al., EMBO Rep., 4(6): 602-608 (2003).
Domitrovich and Kunkel, Nucl. Acids Res., 31(9): 2344-52 (2003).
Boden et al., Nucl. Acids Res., 31(17): 5033-38 (2003a).
Kawasaki et al., Nucleic Acids Res., 31(2): 700-7 (2003).

* cited by examiner

REPORTER CONSTRUCT

SEQUENCE LISTING

```
<160> NUMBER OF SEQ ID NOS: 57

<210> SEQ ID NO 1
<211> LENGTH: 20
<212> TYPE: DNA
<213> ORGANISM: Artificial
<220> FEATURE:
<223> OTHER INFORMATION: oligonucleotide

<400> SEQUENCE: 1

gctgtgagga actactgtct                                                20


<210> SEQ ID NO 2
<211> LENGTH: 19
<212> TYPE: DNA
<213> ORGANISM: Artificial
<220> FEATURE:
<223> OTHER INFORMATION: oligonucleotide

<400> SEQUENCE: 2

gtctagccat ggcgttagt                                                 19


<210> SEQ ID NO 3
<211> LENGTH: 19
<212> TYPE: DNA
<213> ORGANISM: Artificial
<220> FEATURE:
<223> OTHER INFORMATION: oligonucleotide

<400> SEQUENCE: 3

ggagagccat agtggtctg                                                 19


<210> SEQ ID NO 4
<211> LENGTH: 19
<212> TYPE: DNA
<213> ORGANISM: Artificial
<220> FEATURE:
<223> OTHER INFORMATION: oligonucleotide

<400> SEQUENCE: 4

gcggaaccgg tgagtacac                                                 19


<210> SEQ ID NO 5
<211> LENGTH: 20
<212> TYPE: DNA
<213> ORGANISM: Artificial
<220> FEATURE:
<223> OTHER INFORMATION: oligonucleotide

<400> SEQUENCE: 5

gtctgcggaa ccggtgagta                                                20


<210> SEQ ID NO 6
<211> LENGTH: 20
<212> TYPE: DNA
<213> ORGANISM: Artificial
<220> FEATURE:
<223> OTHER INFORMATION: oligonucleotide

<400> SEQUENCE: 6

gcgaaaggcc ttgtggtact                                                20


<210> SEQ ID NO 7
<211> LENGTH: 19
```

-continued

<212> TYPE: DNA
<213> ORGANISM: Artificial
<220> FEATURE:
<223> OTHER INFORMATION: oligonucleotide

<400> SEQUENCE: 7
gatagggtgc ttgcgagtg 19

<210> SEQ ID NO 8
<211> LENGTH: 20
<212> TYPE: DNA
<213> ORGANISM: Artificial
<220> FEATURE:
<223> OTHER INFORMATION: oligonucleotide

<400> SEQUENCE: 8
gaggtctcgt agaccgtgca 20

<210> SEQ ID NO 9
<211> LENGTH: 20
<212> TYPE: DNA
<213> ORGANISM: Artificial
<220> FEATURE:
<223> OTHER INFORMATION: oligonucleotide

<400> SEQUENCE: 9
gcttgtggta ctgcctgata 20

<210> SEQ ID NO 10
<211> LENGTH: 20
<212> TYPE: DNA
<213> ORGANISM: Artificial
<220> FEATURE:
<223> OTHER INFORMATION: oligonucleotide

<400> SEQUENCE: 10
gctgcctgat agggtgcttg 20

<210> SEQ ID NO 11
<211> LENGTH: 19
<212> TYPE: DNA
<213> ORGANISM: Artificial
<220> FEATURE:
<223> OTHER INFORMATION: oligonucleotide

<400> SEQUENCE: 11
atcactcccc tgtgaggaa 19

<210> SEQ ID NO 12
<211> LENGTH: 19
<212> TYPE: DNA
<213> ORGANISM: Artificial
<220> FEATURE:
<223> OTHER INFORMATION: oligonucleotide

<400> SEQUENCE: 12
actcccctgt gaggaacta 19

<210> SEQ ID NO 13
<211> LENGTH: 19
<212> TYPE: DNA
<213> ORGANISM: Artificial
<220> FEATURE:
<223> OTHER INFORMATION: oligonucleotide

<400> SEQUENCE: 13

-continued cgtctagcca tggcgttag 19

<210> SEQ ID NO 14
<211> LENGTH: 19
<212> TYPE: DNA
<213> ORGANISM: Artificial
<220> FEATURE:
<223> OTHER INFORMATION: oligonucleotide

<400> SEQUENCE: 14
tctagccatg gcgttagta 19

<210> SEQ ID NO 15
<211> LENGTH: 19
<212> TYPE: DNA
<213> ORGANISM: Artificial
<220> FEATURE:
<223> OTHER INFORMATION: oligonucleotide

<400> SEQUENCE: 15
ctagccatgg cgttagtat 19

<210> SEQ ID NO 16
<211> LENGTH: 19
<212> TYPE: DNA
<213> ORGANISM: Artificial
<220> FEATURE:
<223> OTHER INFORMATION: oligonucleotide

<400> SEQUENCE: 16
tgtcgtacag cctccaggc 19

<210> SEQ ID NO 17
<211> LENGTH: 19
<212> TYPE: DNA
<213> ORGANISM: Artificial
<220> FEATURE:
<223> OTHER INFORMATION: oligonucleotide

<400> SEQUENCE: 17
ccgggagagc catagtggt 19

<210> SEQ ID NO 18
<211> LENGTH: 19
<212> TYPE: DNA
<213> ORGANISM: Artificial
<220> FEATURE:
<223> OTHER INFORMATION: oligonucleotide

<400> SEQUENCE: 18
agagccatag tggtctgcg 19

<210> SEQ ID NO 19
<211> LENGTH: 19
<212> TYPE: DNA
<213> ORGANISM: Artificial
<220> FEATURE:
<223> OTHER INFORMATION: oligonucleotide

<400> SEQUENCE: 19
gccatagtgg tctgcggaa 19

<210> SEQ ID NO 20
<211> LENGTH: 19
<212> TYPE: DNA
<213> ORGANISM: Artificial

-continued

```
<220> FEATURE:
<223> OTHER INFORMATION: oligonucleotide

<400> SEQUENCE: 20

ccggtgagta caccggaat                                              19


<210> SEQ ID NO 21
<211> LENGTH: 19
<212> TYPE: DNA
<213> ORGANISM: Artificial
<220> FEATURE:
<223> OTHER INFORMATION: oligonucleotide

<400> SEQUENCE: 21

cggtgagtac accggaatc                                              19


<210> SEQ ID NO 22
<211> LENGTH: 19
<212> TYPE: DNA
<213> ORGANISM: Artificial
<220> FEATURE:
<223> OTHER INFORMATION: oligonucleotide

<400> SEQUENCE: 22

gactgggtcc tttcttgga                                              19


<210> SEQ ID NO 23
<211> LENGTH: 19
<212> TYPE: DNA
<213> ORGANISM: Artificial
<220> FEATURE:
<223> OTHER INFORMATION: oligonucleotide

<400> SEQUENCE: 23

gaccgggtcc tttcttgga                                              19


<210> SEQ ID NO 24
<211> LENGTH: 19
<212> TYPE: DNA
<213> ORGANISM: Artificial
<220> FEATURE:
<223> OTHER INFORMATION: oligonucleotide

<400> SEQUENCE: 24

accgggtcct ttcttggaa                                              19


<210> SEQ ID NO 25
<211> LENGTH: 19
<212> TYPE: DNA
<213> ORGANISM: Artificial
<220> FEATURE:
<223> OTHER INFORMATION: oligonucleotide

<400> SEQUENCE: 25

tgggttgcga aaggccttg                                              19


<210> SEQ ID NO 26
<211> LENGTH: 19
<212> TYPE: DNA
<213> ORGANISM: Artificial
<220> FEATURE:
<223> OTHER INFORMATION: oligonucleotide

<400> SEQUENCE: 26

ttgcgaaagg ccttgtggt                                              19
```

-continued

<210> SEQ ID NO 27
<211> LENGTH: 19
<212> TYPE: DNA
<213> ORGANISM: Artificial
<220> FEATURE:
<223> OTHER INFORMATION: oligonucleotide

<400> SEQUENCE: 27
aggccttgtg gtactgcct 19

<210> SEQ ID NO 28
<211> LENGTH: 19
<212> TYPE: DNA
<213> ORGANISM: Artificial
<220> FEATURE:
<223> OTHER INFORMATION: oligonucleotide

<400> SEQUENCE: 28
tagggtgctt gcgagtgcc 19

<210> SEQ ID NO 29
<211> LENGTH: 19
<212> TYPE: DNA
<213> ORGANISM: Artificial
<220> FEATURE:
<223> OTHER INFORMATION: oligonucleotide

<400> SEQUENCE: 29
cgggaggtct cgtagaccg 19

<210> SEQ ID NO 30
<211> LENGTH: 19
<212> TYPE: DNA
<213> ORGANISM: Artificial
<220> FEATURE:
<223> OTHER INFORMATION: oligonucleotide

<400> SEQUENCE: 30
ggtctcgtag accgtgcat 19

<210> SEQ ID NO 31
<211> LENGTH: 19
<212> TYPE: DNA
<213> ORGANISM: Artificial
<220> FEATURE:
<223> OTHER INFORMATION: oligonucleotide

<400> SEQUENCE: 31
agatcgttgg tggagttta 19

<210> SEQ ID NO 32
<211> LENGTH: 20
<212> TYPE: DNA
<213> ORGANISM: artificial
<220> FEATURE:
<223> OTHER INFORMATION: oligonucleotide

<400> SEQUENCE: 32
gttgggtaag gtcatcgata 20

<210> SEQ ID NO 33
<211> LENGTH: 20
<212> TYPE: DNA
<213> ORGANISM: artificial
<220> FEATURE:
<223> OTHER INFORMATION: oligonucleotide

<400> SEQUENCE: 33
gccgacctca tggggtacat 20

<210> SEQ ID NO 34
<211> LENGTH: 19
<212> TYPE: DNA
<213> ORGANISM: artificial
<220> FEATURE:
<223> OTHER INFORMATION: oligonucleotide

<400> SEQUENCE: 34
ggttgctctt tctctatct 19

<210> SEQ ID NO 35
<211> LENGTH: 19
<212> TYPE: DNA
<213> ORGANISM: artificial
<220> FEATURE:
<223> OTHER INFORMATION: oligonucleotide

<400> SEQUENCE: 35
gggatatgat gatgaactg 19

<210> SEQ ID NO 36
<211> LENGTH: 19
<212> TYPE: DNA
<213> ORGANISM: artificial
<220> FEATURE:
<223> OTHER INFORMATION: oligonucleotide

<400> SEQUENCE: 36
ggatgaaccg gctaatagc 19

<210> SEQ ID NO 37
<211> LENGTH: 19
<212> TYPE: DNA
<213> ORGANISM: artificial
<220> FEATURE:
<223> OTHER INFORMATION: oligonucleotide

<400> SEQUENCE: 37
ggagatgggc ggcaacatc 19

<210> SEQ ID NO 38
<211> LENGTH: 19
<212> TYPE: DNA
<213> ORGANISM: artificial
<220> FEATURE:
<223> OTHER INFORMATION: oligonucleotide

<400> SEQUENCE: 38
gtcttcacgg aggctatga 19

<210> SEQ ID NO 39
<211> LENGTH: 20
<212> TYPE: DNA
<213> ORGANISM: artificial
<220> FEATURE:
<223> OTHER INFORMATION: oligonucleotide

<400> SEQUENCE: 39
gtcaactcct ggctaggcaa 20

<210> SEQ ID NO 40

-continued

```
<211> LENGTH: 20
<212> TYPE: DNA
<213> ORGANISM: artificial
<220> FEATURE:
<223> OTHER INFORMATION: oligonucleotide

<400> SEQUENCE: 40

gtccacagtt actctccagg                                          20


<210> SEQ ID NO 41
<211> LENGTH: 20
<212> TYPE: DNA
<213> ORGANISM: artificial
<220> FEATURE:
<223> OTHER INFORMATION: oligonucleotide

<400> SEQUENCE: 41

gcctcttcaa ctgggcagta                                          20


<210> SEQ ID NO 42
<211> LENGTH: 19
<212> TYPE: DNA
<213> ORGANISM: artificial
<220> FEATURE:
<223> OTHER INFORMATION: oligonucleotide

<400> SEQUENCE: 42

agcttaaact cactccaat                                           19


<210> SEQ ID NO 43
<211> LENGTH: 19
<212> TYPE: DNA
<213> ORGANISM: artificial
<220> FEATURE:
<223> OTHER INFORMATION: oligonucleotide

<400> SEQUENCE: 43

gctccatctt agccctagt                                           19


<210> SEQ ID NO 44
<211> LENGTH: 20
<212> TYPE: DNA
<213> ORGANISM: artificial
<220> FEATURE:
<223> OTHER INFORMATION: oligonucleotide

<400> SEQUENCE: 44

gtccatctta gccctagtca                                          20


<210> SEQ ID NO 45
<211> LENGTH: 19
<212> TYPE: DNA
<213> ORGANISM: artificial
<220> FEATURE:
<223> OTHER INFORMATION: oligonucleotide

<400> SEQUENCE: 45

gtcacggcta gctgtgaaa                                           19


<210> SEQ ID NO 46
<211> LENGTH: 19
<212> TYPE: DNA
<213> ORGANISM: artificial
<220> FEATURE:
<223> OTHER INFORMATION: oligonucleotide

<400> SEQUENCE: 46
```

-continued acggctagct gtgaaaggt 19

<210> SEQ ID NO 47
<211> LENGTH: 19
<212> TYPE: DNA
<213> ORGANISM: artificial
<220> FEATURE:
<223> OTHER INFORMATION: oligonucleotide

<400> SEQUENCE: 47
gctgtgaaag gtccgtgag 19

<210> SEQ ID NO 48
<211> LENGTH: 19
<212> TYPE: DNA
<213> ORGANISM: artificial
<220> FEATURE:
<223> OTHER INFORMATION: oligonucleotide

<400> SEQUENCE: 48
ggtccgtgag ccgcatgac 19

<210> SEQ ID NO 49
<211> LENGTH: 20
<212> TYPE: DNA
<213> ORGANISM: artificial
<220> FEATURE:
<223> OTHER INFORMATION: oligonucleotide

<400> SEQUENCE: 49
gccgcatgac tgcagagagt 20

<210> SEQ ID NO 50
<211> LENGTH: 20
<212> TYPE: DNA
<213> ORGANISM: artificial
<220> FEATURE:
<223> OTHER INFORMATION: oligonucleotide

<400> SEQUENCE: 50
actggcctct ctgcagatca 20

<210> SEQ ID NO 51
<211> LENGTH: 19
<212> TYPE: DNA
<213> ORGANISM: artificial
<220> FEATURE:
<223> OTHER INFORMATION: oligonucleotide

<400> SEQUENCE: 51
tagccctagt cacggctag 19

<210> SEQ ID NO 52
<211> LENGTH: 19
<212> TYPE: DNA
<213> ORGANISM: artificial
<220> FEATURE:
<223> OTHER INFORMATION: oligonucleotide

<400> SEQUENCE: 52
agctgtgaaa ggtccgtga 19

<210> SEQ ID NO 53
<211> LENGTH: 19
<212> TYPE: DNA

-continued

```
<213> ORGANISM: artificial
<220> FEATURE:
<223> OTHER INFORMATION: oligonucleotide

<400> SEQUENCE: 53

tagctgtgaa aggtccgtg                                              19


<210> SEQ ID NO 54
<211> LENGTH: 19
<212> TYPE: DNA
<213> ORGANISM: artificial
<220> FEATURE:
<223> OTHER INFORMATION: oligonucleotide

<400> SEQUENCE: 54

ctagctgtga aaggtccgt                                              19


<210> SEQ ID NO 55
<211> LENGTH: 19
<212> TYPE: DNA
<213> ORGANISM: artificial
<220> FEATURE:
<223> OTHER INFORMATION: oligonucleotide

<400> SEQUENCE: 55

ctgtgaaagg tccgtgagc                                              19


<210> SEQ ID NO 56
<211> LENGTH: 19
<212> TYPE: DNA
<213> ORGANISM: artificial
<220> FEATURE:
<223> OTHER INFORMATION: oligonucleotide

<400> SEQUENCE: 56

gaaaggtccg tgagccgca                                              19


<210> SEQ ID NO 57
<211> LENGTH: 171
<212> TYPE: DNA
<213> ORGANISM: artificial
<220> FEATURE:
<223> OTHER INFORMATION: oligonucleotide

<400> SEQUENCE: 57

ggatccgtgc acggtctacg agacctcgaa gcttggaggt ctcgtagacc gtgcatgtac     60

agcgaaaggc cttgtggtac tgaagcttga gtaccacaag gcctttcgcc catggattgg    120

agtgagttta agctgaagct tgagcttaaa ctcactccaa tttttctag a              171
```

RNAI EXPRESSION CONSTRUCTS

CROSS-REFERENCE TO RELATED APPLICATIONS

This application claims benefit of U.S. provisional patent application Ser. No. 60/649,641, filed Feb. 3, 2005 and U.S. provisional patent application Ser. No. 60/653,580, filed Feb. 15, 2005, which are herein incorporated by reference.

BACKGROUND OF THE INVENTION

Utilization of double-stranded RNA to inhibit gene expression in a sequence-specific manner has revolutionized the drug discovery industry. In mammals, RNA interference, or RNAi, is mediated by 15- to 49-nucleotide long, double-stranded RNA molecules referred to as small interfering RNAs (RNAi agents). RNAi agents can be synthesized chemically or enzymatically outside of cells and subsequently delivered to cells (see, e.g., Fire, et al., *Nature,* 391: 806-11 (1998); Tuschl, et al., *Genes and Dev.,* 13:3191-97 (1999); and *Elbashir*, et al., Nature, 411:494-498 (2001)); or can be expressed in vivo by an appropriate vector in cells (see, e.g., U.S. Pat. No. 6,573,099).

In vivo delivery of unmodified RNAi agents as an effective therapeutic for use in humans faces a number of technical hurdles. First, due to cellular and serum nucleases, the half life of RNA injected in vivo is only about 70 seconds (see, e.g., Kurreck, *Eur. J. Bioch.* 270:1628-44 (2003)). Efforts have been made to increase stability of injected RNA by the use of chemical modifications; however, there are several instances where chemical alterations led to increased cytotoxic effects. In one specific example, cells were intolerant to doses of an RNAi duplex in which every second phosphate was replaced by phosphorothioate (Harborth, et al., *Antisense Nucleic Acid Drug Rev.* 13(2): 83-105 (2003)). Other hurdles include providing tissue-specific delivery, as well as being able to deliver the RNAi agents in amounts sufficient to elicit a therapeutic response, but that are not toxic.

Several options are being explored for RNAi delivery, including the use of viral-based and non-viral based vector systems that can infect or otherwise transfect target cells, and deliver and express RNAi molecules in situ. Often, small RNAs are transcribed as short hairpin RNA (shRNA) precursors from a viral or non-viral vector backbone. Once transcribed, the shRNA are hypothesized to be processed by the enzyme Dicer into the appropriate active RNAi agents. Viral-based delivery approaches attempt to exploit the targeting properties of viruses to generate tissue specificity and once appropriately targeted, rely upon the endogenous cellular machinery to generate sufficient levels of the RNAi agents to achieve a therapeutically effective dose.

One useful application of RNAi therapeutics is as an antiviral agent. In general, RNA viruses depend on RNA dependent RNA polymerase for replication. This RNA polymerase replicates the viral genome with comparatively low fidelity, the functional consequence of which produces genomes with an exceptionally high number of mutations. This rapidly results in generations of evolved progeny virions that evade common immunological and chemical antiviral agents. Thus, similar to the effects observed with small molecule therapeutics, the relative potency and efficacy of the RNAi therapeutic may decrease as a result of viral evolution during long term treatment. In one study, HIV escape mutants that contained a single nucleotide change appeared 35 days after delivery of an expressed shRNA (Boden, et al., *J. Virol.* 77(21): 11531-11535 (2003)). In another study, poliovirus escape mutants could be detected in as little as 54 hours post-infection in cells that had been transfected with pre-synthesized RNAi (Gitlin et al J Virol. 2005 January; 79(2):1027-35). Likewise other putative RNAi targets, such as genes involved in cancer have sequence variability. Simultaneous delivery of two of more RNAis against multiple sequences would allow for more effective treatment of any disease that capitalizes on genetic variability to resist inhibition. There is a need in the art to develop stable, effective, expressed RNAi agents that can deliver multiple RNAi agents. The present invention satisfies this need in the art.

SUMMARY OF THE INVENTION

The present invention is directed to genetic constructs for delivering RNAi agents to tissues, organs, or cells to treat various disease or disorders. In one aspect, the present invention provides innovative nucleic acid molecules comprising two or more RNAi agents for modifying target gene expression. In another aspect, the present invention provides an expression cassette (hereinafter referred to as a 1-x RNA expression cassette) comprising a promoter and two or more stem-loop structures separated from one another by a spacer structure. A further aspect of the present invention provides a genetic construct that is capable of modifying expression one or more genes where the genetic construct comprises two or more RNAi agents transcribed from a single promoter. Also, other aspects of the present invention include methods of treating a disease or disorder in a tissue, cell or organ by expressing two or more RNAi agents from a single promoter to modify gene expression in cells tissue or organ.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

DETAILED DESCRIPTION

Figure 1:
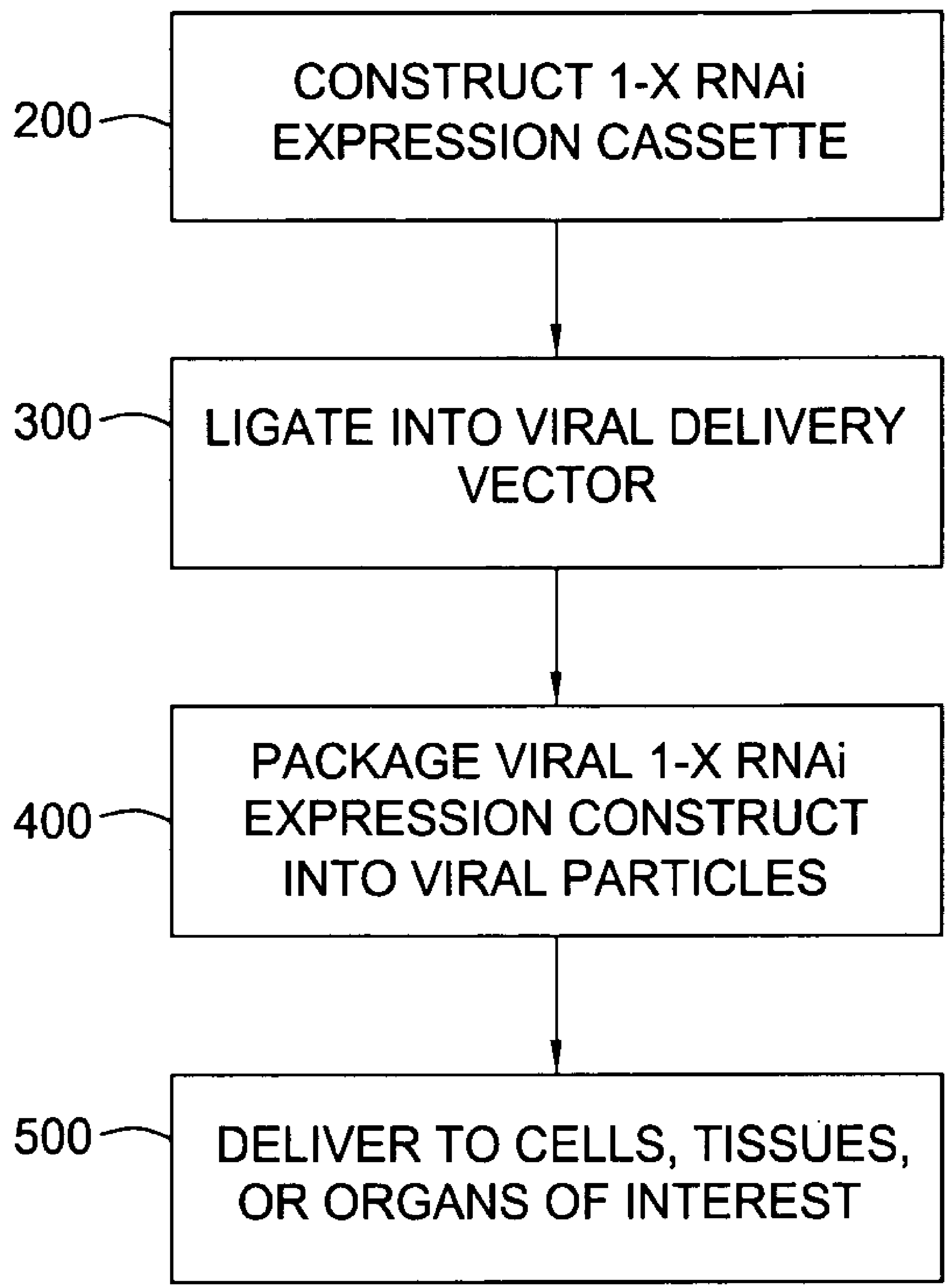
FIG. 1 is a simplified block diagram of one embodiment of a method for delivering 1-x RNAi expression cassettes to cells, tissues or organs of interest according to the present invention.

Before the present compositions and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

As used herein, the singular forms "a," "an," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference, without limitation, for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The present invention is directed to innovative, robust genetic compositions and methods to treat diseases or disorders using novel RNAi cassettes.

Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, *Molecular Cloning: A Laboratory Manual* (1982); *DNA Cloning: A Practical Approach*, Volumes I and II (D. N. Glover, ed. 1985); *Oligonucleotide Synthesis* (M. J. Gait, ed. 1984); *Nucleic Acid Hybridization* (B. D. Hames & S. J. Higgins, eds. (1984)); *Animal Cell Culture* (R. I. Freshney, ed. 1986); and *RNA Viruses: A Practical Approach*, (Alan, J. Cann, Ed., Oxford University Press, 2000).

A "vector" is a replicon, such as plasmid, phage, viral construct or cosmid, to which another DNA segment may be attached. Vectors are used to transduce and express the DNA segment in cells. The terms "construct" and "1-x RNAi expression construct" refer generally to a vector in combination with a 1-x RNAi expression cassette.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase.

A cell has been "transformed", "transduced" or "transfected" by an exogenous or heterologous nucleic acid or vector when such nucleic acid has been introduced inside the cell, for example, as a complex with transfection reagents or packaged in viral particles. The transforming DNA may or may not be integrated (covalently linked) into the genome of the cell. With respect to eukaryotic cells, a stably transformed cell is one in which the transforming DNA has become integrated into a host cell chromosome or is maintained extra-chromosomally so that the transforming DNA is inherited by daughter cells during cell replication or is a non-replicating, differentiated cell in which a persistent episome is present.

The term "RNA interference" or "RNAi" refers generally to a process in which a double-stranded RNA molecule changes the expression of a nucleic acid sequence with which the double-stranded or short hairpin RNA molecule shares substantial or total homology. The term "RNAi agent" refers to an RNA sequence that elicits RNAi; and the term "ddRNAi agent" refers to an RNAI agent that is transcribed from a vector. The terms "short hairpin RNA" or "shRNA" refer to an RNA structure having a duplex region and a loop region. In some embodiments of the present invention, ddRNAi agents are expressed initially as shRNAs. The term "1-x RNAi expression cassette" refers to a cassette according to embodiments of the present invention having one promoter and x RNAi constructs where x is two or three or four or five or more resulting in 1-2, 1-3, 1-4, 1-5, etc. RNAi expression cassettes. The RNAi agents are expressed initially as shRNAs and comprise two or more stem-loop structures separated by one or more spacer region(s). The terms "1-x RNAi expression construct" or "1-x RNAi expression vector" refer to the vectors containing a 1-x RNAi expression cassette.

"Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

FIG. 1 is a simplified flow chart showing the steps of a method according to one embodiment of the present invention in which an 1-x RNAi expression construct may be used. The method includes a step 200 in which the 1-x RNAi expression cassette targeting diseases or disorders is constructed. Next, in step 300, the 1-x RNAi expression cassette is ligated into an appropriate viral delivery construct. The viral 1-x RNAi expression delivery construct is then packaged into viral particles at step 400, and the viral particles are delivered to the cells, tissues or organs of interest at step 500. Details for each of these steps and the components involved are presented infra.

Viral-based 1-x RNAi expression constructs according to the present invention can be generated synthetically or enzymatically by a number of different protocols known to those of skill in the art and purified using standard recombinant DNA techniques as described in, for example, Sambrook et al., *Molecular Cloning: A Laboratory Manual,* 2nd Ed., Cold Spring Harbor Press, Cold Spring Harbor, N.Y. (1989), and under regulations described in, e.g., United States Dept. of HHS, National Institute of Health (NIH) Guidelines for Recombinant DNA Research.

Figure 2A:
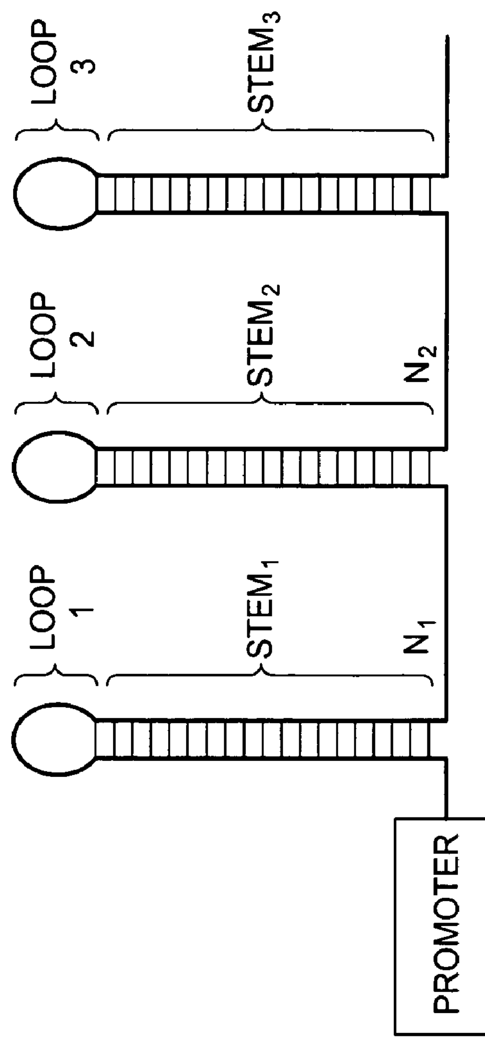
FIGS. 2A, 2B, and 2C show three embodiments of 1-x RNAi expression cassettes according to the present invention.
Figure 2B:
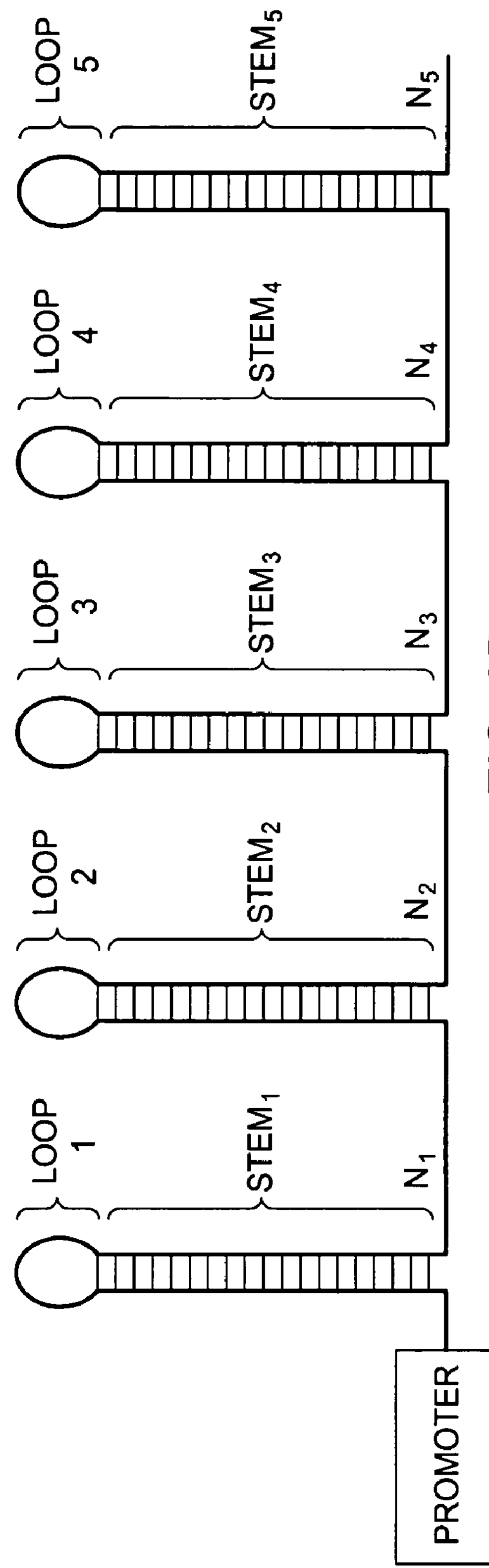
Figure 2C:
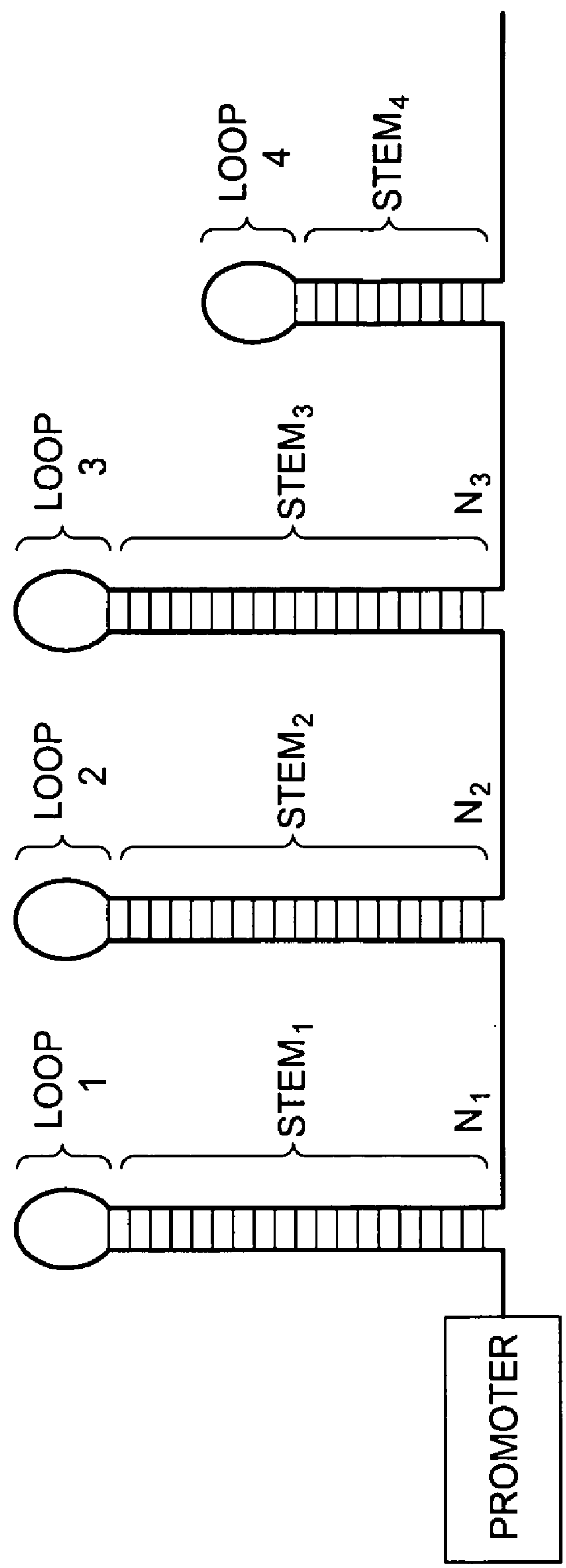

FIGS. 2A and 2B are simplified schematics of 1-3 and 1-5 RNAi expression cassettes according to embodiments of the present invention containing three and five distinct RNAi stem-loop structures respectively. It should be understood by those skilled in the art that 1-x RNAi expression cassettes of the present invention may contain two, four, six or more stem-loop structures and that the embodiments shown in this figure are exemplary. The figures show embodiments of the 1-3 and 1-5 RNAi expression cassettes comprising three and five stem-loop structures separated by spacer regions. The stem regions 1-5 comprise between about 17-21 base pairs, preferably 19 base pairs. The loop regions 1-5 comprise between about 3-20 nucleotides, preferably 5 to 9 nucleotides, more preferably 6 nucleotides. The spacer regions ($N_1$, $N_{2 \ldots}$) between RNAi stems are between about 4-10 nucleotides, preferably 6 nucleotides. FIG. 2C shows a particular embodiment of 1-x RNAi cassettes of this invention comprising three stem-loop structures containing between 17-21 base pairs and a fourth stem-loop structure with a shorter stem region containing between 2-17 base pairs.

An example of a sequence of a multiple hairpin cassette of this invention is the following:

```
ggatccGTGCACGGTCTACGAGACCTCgaagctt (SEQ ID NO. 57)
gGAGGTCTCGTAGACCGTGCAtgtacaGCGAAAG
GCCTTGTGGTACTgaagcttgAGTACCACAAGGC
CTTTCGCccatggATTGGAGTGAGTTTAAGCTga
agcttgAGCTTAAACTCACTCCAATtttttctag
a.
```

When employing a 1-x RNAi expression cassette, the two or more RNAi agents comprising a cassette all have different sequences; that is RNAi1, RNAi2, RNAi3, RNAi4 and RNAi5, for example are all different from one another. Further, in a preferred embodiment, the promoter element and termination element used in the 1-x RNAi expression cassette are matched to each other; that is, the promoter and terminator elements are taken from the same gene in which they occur naturally. Promoters also may or may not be modified using molecular techniques, or otherwise, e.g., through regulation elements, to attain weaker levels of transcription.

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., brain). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue (see, e.g., Higashibata, et al., *J. Bone Miner. Res*. Jan 19(1):78-88 (2004); Hoggatt, et al., *Circ. Res*., Dec. 91(12): 1151-59 (2002); Sohal, et al., *Circ. Res*. Jul 89(1):20-25 (2001); and Zhang, et al., *Genome Res*. Jan 14(1):79-89 (2004)). The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe the RNAi agents preferably are constitutive promoters, such as the promoters for ubiquitin, CMV, β-actin, histone H4, EF-1alfa or pgk genes controlled by RNA polymerase II, or promoter elements controlled by RNA polymerase I. In other embodiments, a Pol II promoter such as CMV, SV40, U1, β-actin or a hybrid Pol II promoter is employed. In other embodiments, promoter elements controlled by RNA polymerase III are used, such as the U6 promoters (U6-1, U6-8, U6-9, e.g.), H1 promoter, 7SL promoter, the human Y promoters (hY1, hY3, hY4 (see Maraia, et al., *Nucleic Acids Res* 22(15):3045-52 (1994)) and hY5 (see Maraia, et al., *Nucleic Acids Res* 24(18):3552-59 (1994)), the human MRP-7-2 promoter, Adenovirus VA1 promoter, human tRNA promoters, the 5s ribosomal RNA promoters, as well as functional hybrids and combinations of any of these promoters.

Alternatively in some embodiments it may be optimal to select promoters that allow for inducible expression of the multiple RNAi agents contained in the 1-x RNAi expression cassette. A number of systems for inducible expression using such promoters are known in the art, including but not limited to the tetracycline responsive system and the lac operator-repressor system (see WO 03/022052 A1 Publication; and U.S. Patent Publication 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

One or more enhancers also may be present in the 1-x RNAi expression construct to increase expression of the gene of interest. Enhancers appropriate for use in embodiments of the present invention include the Apo E HCR enhancer, the CMV enhancer that has been described recently (see, Xia et al, *Nucleic Acids Res* 31-17 (2003)), and other enhancers known to those skilled in the art.

The 1-x RNAi expression cassettes delivering the RNAi agents utilized in the present invention have two or more stem-loop structures in which the ends of the double-stranded RNA of each stem are connected by a single-stranded, loop RNA. The RNAi sequences encoded by the 1-x RNAi expression cassettes of the present invention result in the expression of small interfering RNAs that are short, double-stranded RNAs that are not toxic in normal mammalian cells. There is no particular limitation in the length of the 1-x RNAi expression cassettes of the present invention as long as they do not show cellular toxicity. RNAis can be 17 to 21 bp in length, and are more preferably 19 bp in length. The double-stranded or stem portions of the RNAis may be completely homologous, or may contain non-paired portions due to sequence mismatch (the corresponding nucleotides on each strand are not complementary), bulges (lack of a corresponding complementary nucleotide on one strand), and the like. Such non-paired portions can be tolerated to the extent that they do not significantly interfere with RNAi duplex formation or efficacy. The length of the single-stranded loop portion of the shRNA may be 3 to 20 nucleotides in length, and is preferably 5 to 9 nucleotides in length.

The sequence of the stem structures of the two or more RNAi agents in the expression cassette of the present invention may be the same or different, but the sequences of the RNAi agents in each 1-x expression cassette are most frequently different from one another. Also the length of the stems and the loops of the different RNAi agents in the 1-x RNAi expression cassette may have the same or different length as the other stems and/or other loops in the 1-x RNAi cassette. The two or more stem-loop structures of the present invention are separated by spacer regions. The spacer region is comprised of nucleotides, either naturally occurring or synthetic. The length of the spacer regions between the stem-loop structures may be about 4 to 10 nucleotides, and is preferably about 6 nucleotides. The spacer regions between three or more RNAi agents in the expression cassette of the present invention may have the same sequence or have different sequences and may be of the same or different length.

The nucleic acid sequences that are targets for the 1-x RNAi expression cassettes of the present invention include viral genes, oncogenes, bacterial genes, developmental genes and are selected based upon the genetic sequence of the gene sequence(s); and preferably are based on regions of the gene sequences that are conserved. Methods of alignment of sequences for comparison and RNAi sequence selection are well known in the art. The determination of percent identity between two or more sequences can be accomplished using a mathematical algorithm. Preferred, non-limiting examples of such mathematical algorithms are the algorithm of Myers and Miller (1988); the search-for-similarity-method of Pearson and Lipman (1988); and that of Karlin and Altschul (1993). Preferably, computer implementations of these mathematical algorithms are utilized. Such implementations include, but are not limited to: CLUSTAL in the PC/Gene program (available from Intelligenetics, Mountain View, Calif.); the ALIGN program (Version 2.0), GAP, BESTFIT, BLAST, FASTA, Megalign (using Jotun Hein, Martinez, Needleman-Wunsch algorithms), DNAStar Lasergene and TFASTA in the Wisconsin Genetics Software Package, Version 8 (available from Genetics Computer Group (GCG), 575 Science Drive, Madison, Wis., USA). Alignments using these programs can be performed using the default parameters or parameters selected by the operator. The CLUSTAL program is well described by Higgins. The ALIGN program is based on the algorithm of Myers and Miller; and the BLAST programs are based on the algorithm of Karlin and Altschul. Software for performing BLAST analyses is publicly available through the National Center for Biotechnology Information.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Typically, inhibition of target sequences by RNAi requires a high degree of sequence homology between the target sequence and the sense strand of the RNAi molecules. In some embodiments, such homology is higher than about 70%, and may be higher than about 75%. Preferably, homology is higher than about 80%, and is higher than 85% or even 90%. More preferably, sequence homology between the target sequence and the sense strand of the RNAi is higher than about 90%, 91%, 92%, 93%, 94%, 95%, 96%, 97%, 98% or 99%.

In embodiments where the 1-x RNAi expression construct is used to target viral infections, it may be that sequence homology between the genomes of the various subspecies of the virus, even in conserved regions, does not reach the level of over 90% or even 80% over 15 to 30 consecutive nucleotides. In such a case, sequence homology between the target sequence for some subspecies and the sense strand of the RNAi may be 80% or less. On the other hand, the 1-x RNAi expression construct embodiments of the present invention are particularly useful when targeting genes of organisms that do not display high sequence homology across species, subspecies or variants, as each ddRNAi agent in the 1-x RNAi expression cassette can be used to address different portions of the target gene(s) or subsets of variants, subspecies or varying allelic sequences.

A major problem of current anti-viral therapies is the emergence of resistant variants, known generally as escape mutants (Gitlin et. al. *J. of Virol.* 79; 1027-1035, 2005). One aspect of the present invention neutralizes emergent escape mutants. In some embodiments of this invention the selection of multiple RNAi sequences to treat viral infections are chosen based on the emergence of escape mutants from treatment of infected cells single sequence of RNAi. Emergent escape mutants are determined by treatment with an expression construct containing a single sequence of RNAi after the cells have been infected with virus. Cells containing resistant viruses that emerge are harvested and the viral genomes sequenced. Sequencing reveals predominant mutations that arise to resist viral inhibition. A 1-x RNAi expression construct of the present invention is generated that contains RNAi sequences based upon the genetic sequence of the target gene and additionally sequences of the point mutations that arise to resist RNAi treatment.

In addition to selecting the RNAi sequences based on conserved regions of a gene, selection of the RNAi sequences may be based on other factors. Despite a number of attempts to devise selection criteria for identifying sequences that will be effective in RNAi based on features of the desired target sequence (e.g., percent GC content, position from the translation start codon, or sequence similarities based on an in silico sequence database search for homologs of the proposed RNAi, thermodynamic pairing criteria), it is presently not possible to predict with much degree of confidence which of the myriad possible candidate RNAi sequences that correspond to a gene, in fact, elicit an optimal RNA silencing response (though this has come along way: Dharmacon claims 70% success rates nowadays). Instead, individual specific candidate RNAi polynucleotide sequences typically are generated and tested to determine whether interference with expression of a desired target can be elicited.

In some embodiments of this invention, the ddRNAi agent coding regions of 1-x RNAi expression cassette are operatively linked to a terminator element. In one embodiment, using pol III promoters, the terminator comprises a stretch of four or more thymidine residues. Other terminators include the SV40 poly A, the Ad VA1 gene, the 5S ribosomal RNA gene, and human t-RNAs. In addition, the promoter and terminator may be mixed and matched, as is commonly done with RNA pol II promoters and terminators.

In addition, the 1-x RNAi expression cassettes may be configured where multiple cloning sites and/or unique restriction sites are located strategically, such that the promoter, ddRNAi agents and terminator elements are easily removed or replaced. The 1-x RNAi expression cassettes may be assembled from smaller oligonucleotide components using strategically located restriction sites and/or complementary sticky ends. The base vector for one approach according to embodiments of the present invention consists of plasmids with a multilinker in which all sites are unique (though this is not an absolute requirement). Sequentially, a promoter is inserted between its designated unique sites resulting in a base cassette with a promoter that can have variable orientation. Sequentially, annealed primer pairs are inserted into the unique sites downstream of the individual resulting in a single, double- or multiple-1-x RNAi expression cassette construct. The insert can be moved into, e.g. a vector backbone using two unique enzyme sites (the same or different ones) that flank the single, double- or multiple-1-x RNAi expression cassette insert.

In step 300 of FIG. 1, the 1-x RNAi expression cassette is ligated into a delivery vector. The vectors into which the 1-x RNAi expression cassette is inserted and used for high efficiency transduction and expression of the 1-x RNAi expression cassette in various cell types may be derived from viruses and are compatible with viral delivery; alternatively, a non-viral vector may be used. Generation of the resulting construct comprising the vector and the 1-x RNA expression cassette can be accomplished using any suitable genetic engineering techniques well known in the art, including without limitation, the standard techniques of PCR, oligonucleotide synthesis, restriction endonuclease digestion, ligation, transformation, plasmid purification, and DNA sequencing. If the construct is a based on a viral construct, the vector preferably comprises, for example, sequences necessary to package the 1-x RNAi expression construct into viral particles and/or sequences that allow integration of the 1-x RNAi expression construct into the target cell genome. The viral construct also may contain genes that allow for replication and propagation of virus, though in other embodiments such genes will be supplied in trans. Additionally, the viral construct may contain genes or genetic sequences from the genome of any known organism incorporated in native form or modified. For example, a preferred viral construct may comprise sequences useful for replication of the construct in bacteria.

The construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the 1-x RNAi expression cassette, an internal ribosomal entry site (IRES) sequence can be included. Preferably, the additional genetic elements are operably linked with and controlled by an independent promoter/enhancer. In addition a suitable origin of replication for propagation of the construct in bacteria may be employed. The sequence of the origin of replication generally is separated from the 1-x expression cassette and other genetic sequences that are to be expressed in the cell, tissue, or organ of interest. Such origins of replication are known in the art and include the pUC, ColE1, 2-micron or SV40 origins of replication.

A viral delivery system based on any appropriate virus may be used to deliver the 1-x RNAi expression constructs of the present invention. In addition, hybrid viral systems may be of use. The choice of viral delivery system will depend on various parameters, such as efficiency of delivery into the cell, tissue, or organ of interest, transduction efficiency of the system, pathogenicity, immunological and toxicity concerns, and the like. It is clear that there is no single viral system that is suitable for all applications. When selecting a viral delivery system to use in the present invention, it is important to choose a system where 1-x RNAi expression construct-containing viral particles are preferably: 1) reproducibly and stably propagated; 2) able to be purified to high titers; and 3) able to mediate targeted delivery (delivery of the 1-x RNAi expression construct to the cell, tissue, or organ of interest, without widespread dissemination).

In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). Integrating vectors are the tools of choice if stable genetic alteration needs to be maintained in actively dividing cells.

For example, in one embodiment of the present invention, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transducer a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai, et al., *J. Virol.* 76:11343-349 (2002). Expression of the transgene can be exceptionally stable and in one study with AAV delivery of Factor IX, a dog model continues to express therapeutic levels of the protein over 5.0 years after a single direct infusion with the virus. Because progeny virus is not produced from AAV infection in the absence of helper virus, the extent of transduction is restricted only to the initial cells that are infected with the virus. It is this feature which makes AAV a preferred gene therapy vector for the present invention. Furthermore, unlike retrovirus, adenovirus, and herpes simplex virus, AAV appears to lack human pathogenicity and toxicity (Kay, et al., *Nature.* 424: 251 (2003) and Thomas, et al., *Nature Reviews, Genetics* 4:346-58 (2003)).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order produce the proteins needed to replicate and package the AAV-based heterologous construct into nascent virion, the rep and cap proteins must be provided in trans. The helper functions normally provided by co-infection with the helper virus, such as adenovirus or herpesvirus mentioned above also can be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as RNAi.

The utility of AAV for RNAi applications was demonstrated in experiments where AAV was used to deliver shRNA in vitro to inhibit p53 and Caspase 8 expression (Tomar et al., *Oncogene.* 22: 5712-15 (2003)). Following cloning of the appropriate sequences into a gutted AAV-2 vector, infectious AAV virions were generated in HEK293 cells and used to infect HeLa S3 cells. A dose-dependent decrease of endogenous Caspase 8 and p53 levels was demonstrated. Boden et al. also used AAV to deliver shRNA in vitro to inhibit HIV replication in tissue culture systems (Boden, et al., *J. Virol.* 77(21): 115231-35 (2003)) as assessed by p24 production in the spent media.

However, technical hurdles must be addressed when using AAV as a vehicle for 1-x RNAi expression constructs. For example, various percentages of the human population may possess neutralizing antibodies against certain AAV serotypes. However, since there are several AAV serotypes, for some of which the percentage of individuals harboring neutralizing antibodies is vastly reduced, other serotypes can be used or pseudo-typing may be employed. There are at least ten different serotypes (see De et al Mol Ther. 2006 January; 13(l):67-76) that have been characterized, with dozens of others which have been isolated but have been less well described. Another limitation is that as a result of a possible immune response to AAV, AAV-based therapy may only be administered once; however, use of alternate, non-human derived serotypes may allow for repeat administrations. Administration route, serotype, and composition of the delivered genome all influence tissue specificity (see for instance Zhu et al Circulation. 2005 Oct. 25; 112(17):2650-9).

Another limitation in using unmodified AAV systems with the 1-x RNAi expression constructs is that transduction can be inefficient. Stable transduction in vivo may be limited to 5-10% of cells. However, different methods are known in the art to boost stable transduction levels. One approach is utilizing pseudotyping, where AAV-2 genomes are packaged using cap proteins derived from other serotypes. For example, by substituting the AAV-5 cap gene for its AAV-2 counterpart, Mingozzi et al. increased stable transduction to approximately 15% of hepatocytes (Mingozzi, et al., *J. Virol.* 76(20): 10497-502 (2002)). Thomas et al., transduced over 30% of mouse hepatocytes in vivo using the AAV8 capsid gene (Thomas, et al., J Virol. 2004 March; 78(6):3110-22). Grimm et al. (*Blood.* 2003-02-0495) exhaustively pseudotyped AAV-2 with AAV-1, AAV-3B, AAV-4, AAV-5, and AAV-6 for tissue culture studies. The highest levels of transgene expression were induced by virion which had been pseudotyped with AAV-6; producing nearly 2000% higher transgene expression than AAV-2. Thus, the present invention contemplates use of a pseudotyped AAV virus to achieve high transduction levels, with a corresponding increase in the expression of the 1-x RNAi expression constructs.

Self complementary AAV vectors may also be used according to embodiments of the invention. The most significant distinction between a standard AAV vector and a self complementary vector is in the form of its genome and the size packaged. A standard AAV vector has 4.6 Kb of single stranded DNA while a self complementary AAV vector has 2.3 Kb of double stranded DNA. An AAV vector can be converted into a self complementary vector by introducing a mutation/deletion in one of the inverted terminal repeats (ITR). Each AAV genome has two such repeats at the 5' and 3' ends. Replication typically starts at one of the ITRs and commences through the genome and resolves at the other ITR. It is for this reason that AAV vectors contain genomes that are either positive or negative stranded. The sequences that govern transcriptional resolution most definitively are the D-sequence and the terminal resolution site (trs). These sequences sit between nucleotides 122-144 of the AAV2 genome (Wang et al (2003) Gene Therapy 10: 2106-2111) and deletion of them disallows transcriptional resolution at an ITR. It should be noted that, since the ITRs of AAV vectors are nearly identical, deletion of the D-sequence and trs can be done in either of the two ITRs. As a result of the ITR D-sequence and trs deletion, an elongating replication complex can no longer resolve, and the complex continues in an orientation opposite to the original direction, i.e. if the replication complex first generated a positive strand, it fails to resolve at the deleted ITR and then generates a negative strand that is complementary to the positive strand. This then results in a self complementary double stranded DNA molecule that will get packaged in the AAV vector provided its length is not over 2.3 kb and is preferably shorter. It should be noted that since ITRs of an AAV vector recombine during the replication process, a revertant phenotype, i.e. both ITRs regaining wild type sequences, may result. In order to alleviate this problem, ITRs of different AAV vectors must be used. For instance an AAV2 Left ITR with an AAV4 deleted Right ITR, etc. The sole criterion that governs the choice of ITRs to be combined lies in the sequence identity between the ITRs of the serotype. The ITRs of serotypes 2 and 5 are nearly identical, and the ITRs of serotypes 2 and 4 have an 81.6% similarity. After deletion of the D sequence and trs, the sequence identify between the ITRs of AAV 2 and AAV 4 drops to just over 50%. The combination of these two ITRs therefore generates a good combination of divergent ITRs and will result in a self complementary AAV vector that can no longer regenerate progeny with wildtype ITRs.

Self complementary vectors have considerable advantages over single stranded vectors in terms of their ability to effectively transduce cells. Pseudotyped with the capsid proteins of AAV8, it has been shown that AAV vectors can transduce upwards of 95% of targeted liver cells (see Nakai et al J Virol. 2005 January; 79(1):214-24 and Grimm et al, J Virol. 2006 January; 80(1):426-39).

Another viral delivery system useful with the 1-x RNAi expression constructs of the present invention is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some embodiments, lentiviruses are the preferred members of the retrovirus family for use in the present invention. Lentivirus vectors are often pseudotyped with vesicular stomatitis virus glycoprotein (VSV-G), and have been derived from the human immunodeficiency virus (HIV), the etiologic agent of the human acquired immunodeficiency syndrome (AIDS); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization.

Reverse transcription of the retroviral RNA genome occurs in the cytoplasm. Unlike C-type retroviruses, the lentiviral cDNA complexed with other viral factors—known as the pre-initiation complex—is able to translocate across the nuclear membrane and transduce non-dividing cells. A structural feature of the viral cDNA—a DNA flap—seems to contribute to efficient nuclear import. This flap is dependent on the integrity of a central polypurine tract (cPPT) that is located in the viral polymerase gene, so most lentiviral-derived vectors retain this sequence. Lentiviruses have broad tropism, low inflammatory potential, and result in an integrated vector. The main limitations are that integration might induce oncogenesis in some applications. The main advantage to the use of lentiviral vectors is that gene transfer is persistent in most tissues or cell types.

A lentiviral-based construct used to express the ddRNAi agents preferably comprises sequences from the 5' and 3' LTRs of a lentivirus. More preferably the viral construct comprises an inactivated or self-inactivating 3' LTR from a lentivirus. The 3' LTR may be made self-inactivating by any method known in the art. In a preferred embodiment, the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the 1-x RNAi expression cassettes of the present invention to cells, tissues or organs of interest, including but not limited to gene-deleted adenovirus-transposon vectors that stably maintain virus-encoded transgenes in vivo through integration into host cells (see Yant, et al., *Nature Biotech.* 20:999-1004 (2002)); systems derived from Sindbis virus or Semliki forest virus (see Perri, et al, *J. Virol.* 74(20):9802-07 (2002)); systems derived from Newcastle disease virus or Sendai virus; or mini-circle DNA vectors devoid of bacterial DNA sequences (see Chen, et al., *Molecular Therapy.* 8(3):495-500 (2003)). Mini-circle DNA as described in U.S. Patent Publication No. 2004/0214329 discloses vectors that provide for persistently high levels of protein. The circular vectors are characterized by being devoid of expression-silencing bacterial sequences, and may include a unidirectional site-specific recombination product sequence in addition to an expression cassette.

In addition, hybrid viral systems may be used to combine useful properties of two or more viral systems. For example, the site-specific integration machinery of wild-type AAV may be coupled with the efficient internalization and nuclear targeting properties of adenovirus. AAV in the presence of adenovirus or herpesvirus undergoes a productive replication cycle; however, in the absence of helper functions, the AAV genome integrates into a specific site on chromosome 19. Integration of the AAV genome requires expression of the AAV rep protein. As conventional rAAV vectors are deleted for all viral genes including rep, they are not able to specifically integrate into chromosome 19. However, this feature may be exploited in an appropriate hybrid system. In addition, non-viral genetic elements may be used to achieve desired properties in a viral delivery system, such as genetic elements that allow for site-specific recombination.

Figure 3A:
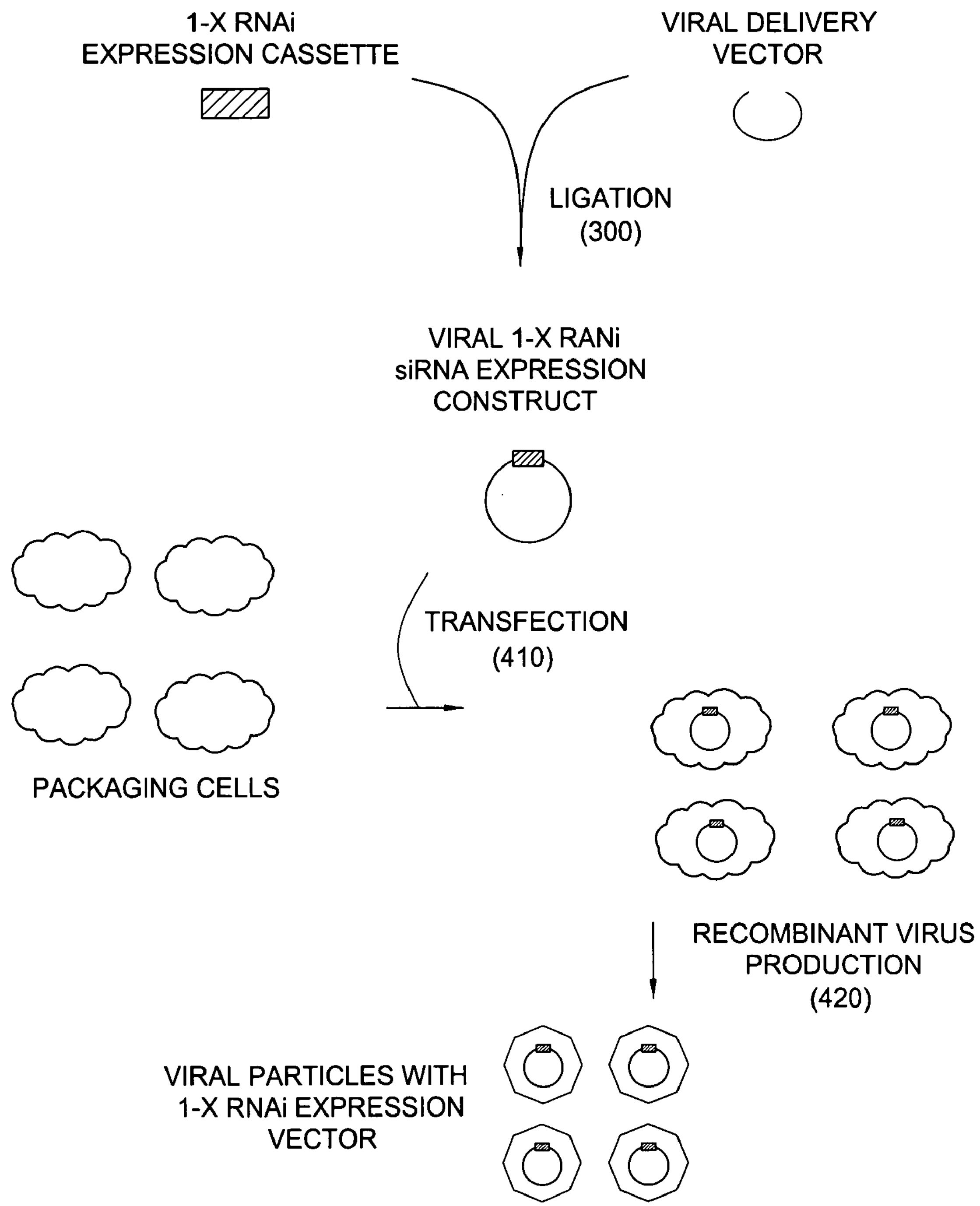
FIGS. 3A and 3B show alternative methods for producing viral particles for delivery of constructs comprising the 1-x RNAi expression cassettes to cells, tissues or organs of interest.
Figure 3B:
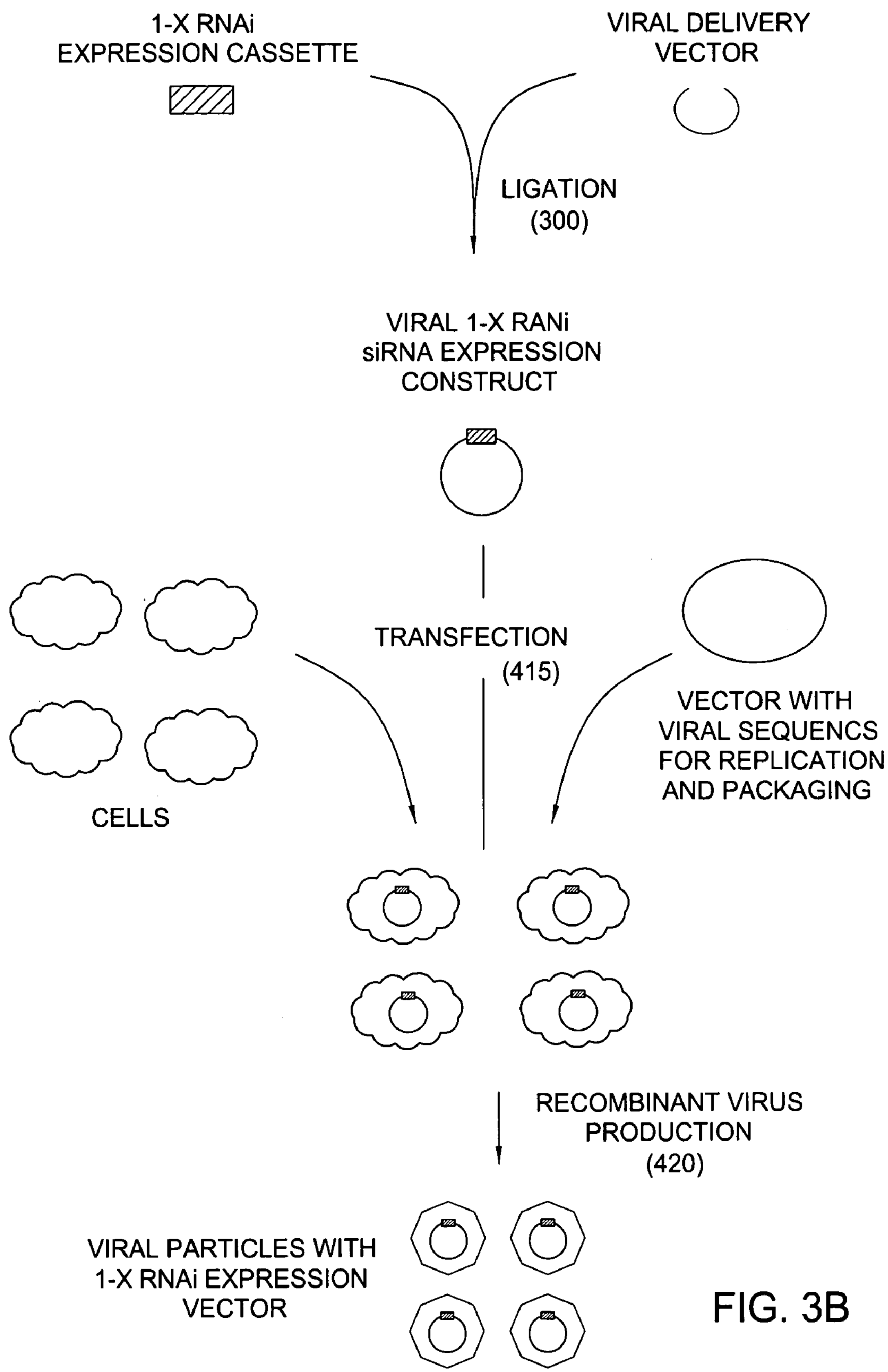

In step 400 of FIG. 1, the 1-x RNAi expression construct is packaged into viral particles. Any method known in the art may be used to produce infectious viral particles whose genome comprises a copy of the viral 1-x RNAi expression construct. FIGS. 3A and 3B show alternative methods for packaging the 1-x RNAi expression constructs of the present invention into viral particles for delivery. The method in FIG. 3A utilizes packaging cells that stably express in trans the viral proteins that are required for the incorporation of the viral 1-x RNAi expression construct into viral particles, as well as other sequences necessary or preferred for a particular viral delivery system (for example, sequences needed for replication, structural proteins and viral assembly) and either viral-derived or artificial ligands for tissue entry. In FIG. 3A, a 1-x RNAi expression cassette is ligated to a viral delivery vector (step 300), and the resulting viral 1-x RNAi expression construct is used to transfect packaging cells (step 410). The packaging cells then replicate viral sequences, express viral proteins and package the viral 1-x RNAi expression constructs into infectious viral particles (step 420). The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with two or more constructs to achieve efficient production of functional particles. One of the constructs comprises the viral 1-x RNAi expression construct, and the other plasmid(s) comprises nucleic acids encoding the proteins necessary to allow the cells to produce functional virus (replication and packaging construct) as well as other helper functions. The method shown in FIG. 3B utilizes cells for packaging that do not stably express viral replication and packaging genes. In this case, the 1-x RNAi expression construct is ligated to the viral delivery vector (step 300) and then co-transfected with one or more vectors that express the viral sequences necessary for replication and production of infectious viral particles (step 415). The cells replicate viral sequences, express viral proteins and package the viral RNAi expression constructs into infectious viral particles (step 420).

The packaging cell line or replication and packaging construct may not express envelope gene products. In these embodiments, the gene encoding the envelope gene can be provided on a separate construct that is co-transfected with the viral 1-x RNAi expression construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells.) In addition, genetically-modified ligands can be used for cell-specific targeting, such as the asialoglycoprotein for hepatocytes, or transferrin for receptor-mediated binding.

After production in a packaging cell line, the viral particles containing the 1-x RNAi expression cassettes are purified and quantified (titered). Purification strategies include density gradient centrifugation, or preferably, column chromatographic methods.

In step 500 of FIG. 1, the 1-x RNAi expression construct is delivered to the cells, tissues, or organs of interest. The 1-x RNAi expression construct of the present invention may be introduced into the cells in vitro or ex vivo and then subsequently placed into an animal to affect therapy, or administered directly to an organism, organ or cell by in vivo administration. Delivery by viral infection is a preferred method of delivery; however, any appropriate method of delivery of the 1-x RNAi expression construct may be employed. The vectors comprising the cassettes can be administered to a mammalian host using any convenient protocol, where a number of different such protocols are known in the art.

The 1-x RNAi expression construct equipped with the appropriate promoter and terminator, e.g. the T7 or T3 phage derived promoters and terminators, or others known to those skilled in the art, may be used for in vitro transcription of the template. Thus, a RNA hairpin molecule of variable length (with 2, 3, 4 or more functional individual hairpins) may be produced in vitro that can be purified and administered as set forth below.

A variety of techniques are available and well known for delivery of nucleic acids into cells, for example liposome- or micelle-mediated transfection or transformation, transformation of cells with attenuated virus particles or bacterial cells, cell mating, transformation or transfection procedures known to those skilled in the art or microinjection.

The most common transfection reagents are charged lipophilic compounds that are capable of crossing cell membranes. When these are complexed with a nucleic acid they can act to carry DNA across the cell membrane. A large number of such compounds are available commercially. Polyethylenimine (PEI) is a new class of transfection reagents, chemically distinct from the lipophilic compounds that act in a similar fashion, but have the advantage they can also cross nuclear membranes. An example of such a reagent is ExGen 500 (Fermentas). A construct or synthetic gene according to the present invention may be packaged as a linear fragment within a synthetic liposome or micelle for delivery into the target cell.

Tissue culture cells can be transformed using electroporation. This is thought to produce transient pores in cell membranes, through which DNA or RNA move into cells. In addition, animal cells can be transformed chemically using reagents such as PEG or calcium phosphate.

Alternatively, ddRNAi expression constructs containing the 1-x RNAi expression cassette may be introduced into cells, tissues or organs of interest by other routes, including microinjection or fusion of vesicles. Injection may also be used for intra-muscular administration, as described by Furth et al., *Anal. Biochem.* 115(205):365-368 (1992). The nucleic acids may be coated onto gold microparticles, and delivered intradermally by a particle bombardment device, or "gene gun" as described in the literature (see, for example, Tang et al., *Nature.* 356:152-154 (1992)), where gold microprojectiles are coated with the DNA, then bombarded into cells, tissues or organs of interest.

Another delivery method useful for the method of this invention comprises the use of Cyclosert™ technology as described in U.S. Pat. No. 6,509,323 to Davis et. al. Cyclosert™ technology platform is based upon cup-shaped cyclic repeating molecules of glucose known as cyclodextrins. The "cup" of the cyclodextrin molecule can form "inclusion complexes" with other molecules, making it possible to combine the Cyclosert™ polymers with other moieties to enhance stability or to add targeting ligands. In addition, cyclodextrins have generally been found to be safe in humans (individual cyclodextrins currently enhance solubility in FDA-approved oral and IV drugs) and can be purchased in pharmaceutical grade on a large scale at low cost. These polymers are extremely water soluble, non-toxic and non-immunogenic at therapeutic doses, even when administered repeatedly. The polymers can easily be adapted to carry a wide range of small-molecule therapeutics at drug loadings that can be significantly higher than liposomes.

The vectors comprising the 1-x RNAi expression cassettes of the present invention can be formulated into preparations for injection or administration by dissolving, suspending or emulsifying them in an aqueous or nonaqueous solvent, such as oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In addition, the vectors comprising the RNAi expression cassettes of the present invention can be formulated into pharmaceutical compositions by combination with appropriate, pharmaceutically acceptable carriers or diluents. In pharmaceutical dosage forms, the vectors comprising the 1-x RNAi cassettes may be administered alone or in association or combination with other pharmaceutically active compounds.

EXAMPLES

To select candidate sequences for target by 1-x RNAi cassettes of this invention, an alignment of all published independent full-length or near-full-length HCV sequences was performed; currently there are about 100 such sequences available representing all genotypes. Several candidate regions for selection and development of RNAi therapeutics currently exist and it is well-documented that the 5' and 3'UTR regions are amongst the most highly conserved regions in the HCV genome. Despite perception that these non-coding sequences may not represent optimal sequences to target due to the potential for steric hindrance with the cellular translation complex proteins or regulatory proteins, Yokota et al. have already identified a highly functional RNAi targeting the 5' UTR in a replicon system (*EMBO Rep.* 4(6): 602-608 (2003)). Although it would be beneficial to identify several regions of absolute identity within individual stretches of 21 nucleotides (the corresponding size of the targeting sequences in a shRNA species), analysis to date demonstrates that such a degree of conservation does not occur within the various subtypes of a specified genotype, let alone across all genotypes. Thus, selection may include segments of the genome in which greater than 80% of the regions maintain absolute conservation. The expression of three independent shRNAs compensates for the sequence variability, allowing for a combination therapy contained within a single delivery vehicle.

Alternatively, if conserved regions that meet the selection criterion in an analysis of all HCV genotypes are not identified, sequence analysis may be restricted to genotype 1 (1a and 1b), which accounts for nearly three quarters of the infected population with the United States and, with the exception of Africa, is the predominate genotype throughout the world. In addition, the most current effective anti-HCV therapy, a combination of pegylated interferon with Ribavirin (a guanosine analogue), is rather inefficient against genotype 1, but highly efficient against the other genotypes. Thus, the greatest need for an alternative therapy exists in the largest patient population. As sequence alignments only reveal homology, other selection criteria, such as relative GC content and the lack of cross specificity when queried against sequence databases, is applied when selecting the final RNAi agents to be tested.

For example, for one experiment, alignment was performed for multiple sequences from HCV subtypes 1a and 1b. A few conserved regions were identified as being long enough from which to select RNAi agents for testing (>19 nucleotides). The 5'NTR and 3'NTR regions were the most conserved regions. Since the regions of homology that were identified were quite long, alignment also was performed between different genotypes. Combining the two alignments allowed selection of universally conserved regions. Some regions, such as long stretches of A's or U's, or of G's and C's were removed from consideration, leaving "qualified" regions for further selection. Only one universally conserved region was identified in the whole coding region (the open reading frame) for all of the genotypes of HCV considered; therefore, the sequences selected for targets in most cases were those that are conserved in subtypes 1a and 1b.

Once "qualified" regions were identified, individual RNAi sequences were selected applying the criterion that the 5' end of the antisense strand in the RNAi agent should possess a lower free energy than the 3' end. "Neighbor pair free energy" rules were applied to calculate free energy for the terminal five nucleotides on both the 5' and 3' ends of all potential RNAi agents selected thus far. As a result, a total of 56 potential RNAi agents were identified: thirty in the 5'NTR (5'-n), twelve in the ORF (c-n), and fourteen in the 3'NTR (3'-n) (see Table 1). The locations of the sequences of SEQ ID NO. 1-10 and 31-50 are pictured schematically in FIG. 7.

TABLE 1

RNAi Sequences

| RNAi agent | Sequence | SEQ ID NO. | Luc-HCV Reporter Plasmid |
|---|---|---|---|
| 5'-1 | gCTGTGAGGAACTACTGTCT | SEQ ID NO. 1 | 20 |
| 5'-2 | GTCTAGCCATGGCGTTAGT | SEQ ID NO. 2 | — |
| 5'-3 | GGAGAGCCATAGTGGTCTG | SEQ ID NO. 3 | 16, 20 |
| 5'-4 | GCGGAACCGGTGAGTACAC | SEQ ID NO. 4 | 16 |
| 5'-5 | GTCTGCGGAACCGGTGAGTA | SEQ ID NO. 5 | 16 |
| 5'-6 | GCGAAAGGCCTTGTGGTACT | SEQ ID NO. 6 | 16, 17 |
| 5'-7 | GATAGGGTGCTTGCGAGTG | SEQ ID NO. 7 | 16 |
| 5'-8 | GAGGTCTCGTAGACCGTGCA | SEQ ID NO. 8 | 16, 17 |
| 5'-9 | gCTTGTGGTACTGCCTGATA | SEQ ID NO. 9 | — |
| 5'-10 | gCTGCCTGATAGGGTGCTTG | SEQ ID NO. 10 | 17 |
| 5'-11 | ATCACTCCCCTGTGAGGAA | SEQ ID NO. 11 | — |
| 5'-12 | ACTCCCCTGTGAGGAACTA | SEQ ID NO. 12 | — |
| 5'-13 | CGTCTAGCCATGGCGTTAG | SEQ ID NO. 13 | — |
| 5'-14 | TCTAGCCATGGCGTTAGTA | SEQ ID NO. 14 | — |
| 5'-15 | CTAGCCATGGCGTTAGTAT | SEQ ID NO. 15 | — |
| 5'-16 | TGTCGTACAGCCTCCAGGC | SEQ ID NO. 16 | — |
| 5'-17 | CCGGGAGAGCCATAGTGGT | SEQ ID NO. 17 | — |
| 5'-18 | AGAGCCATAGTGGTCTGCG | SEQ ID NO. 18 | — |
| 5'-19 | GCCATAGTGGTCTGCGGAA | SEQ ID NO. 19 | — |
| 5'-20 | CCGGTGAGTACACCGGAAT | SEQ ID NO. 20 | |
| 5'-21 | CGGTGAGTACACCGGAATC | SEQ ID NO. 21 | — |
| 5'-22 | GACTGGGTCCTTTCTTGGA | SEQ ID NO. 22 | — |
| 5'-23 | GACCGGGTCCTTTCTTGGA | SEQ ID NO. 23 | — |
| 5'-24 | ACCGGGTCCTTTCTTGGAA | SEQ ID NO. 24 | — |
| 5'-25 | TGGGTTGCGAAAGGCCTTG | SEQ ID NO. 25 | — |
| 5'-26 | TTGCGAAAGGCCTTGTGGT | SEQ ID NO. 26 | — |
| 5'-27 | AGGCCTTGTGGTACTGCCT | SEQ ID NO. 27 | — |
| 5'-28 | TAGGGTGCTTGCGAGTGCC | SEQ ID NO. 28 | — |
| 5'-29 | CGGGAGGTCTCGTAGACCG | SEQ ID NO. 29 | — |
| 5'-30 | GGTCTCGTAGACCGTGCAT | SEQ ID NO. 30 | — |
| C-1 | AGATCGTTGGTGGAGTTTA | SEQ ID NO. 31 | — |
| C-2 | gTTGGGTAAGGTCATCGATA | SEQ ID NO. 32 | — |
| C-3 | GCCGACCTCATGGGGTACAT | SEQ ID NO. 33 | 18 |
| C-4 | GGTTGCTCTTTCTCTATCT | SEQ ID NO. 34 | — |
| C-5 | GGGATATGATGATGAACTG | SEQ ID NO. 35 | — |
| C-6 | GGATGAACCGGCTAATAGC | SEQ ID NO. 36 | — |
| C-7 | GGAGATGGGCGGCAACATC | SEQ ID NO. 37 | — |
| C-8 | GTCTTCACGGAGGCTATGA | SEQ ID NO. 38 | — |
| C-9 | GTCAACTCCTGGCTAGGCAA | SEQ ID NO. 39 | — |
| C-10 | gTCCACAGTTACTCTCCAGG | SEQ ID NO. 40 | — |
| C-11 | gCCTCTTCAACTGGGCAGTA | SEQ ID NO. 41 | — |
| C-12 | AGCTTAAACTCACTCCAAT | SEQ ID NO. 42 | C11&12, C6-C9-C12-3'1 |
| 3'-1 | GCTCCATCTTAGCCCTAGT | SEQ ID NO. 43 | 19 |
| 3'-2 | gTCCATCTTAGCCCTAGTCA | SEQ ID NO. 44 | 19 |
| 3'-3 | GTCACGGCTAGCTGTGAAA | SEQ ID NO. 45 | 19 |
| 3'-4 | ACGGCTAGCTGTGAAAGGT | SEQ ID NO. 46 | 19 |
| 3'-5 | GCTGTGAAAGGTCCGTGAG | SEQ ID NO. 47 | 19 |
| 3'-6 | GGTCCGTGAGCCGCATGAC | SEQ ID NO. 48 | — |

TABLE 1-continued

RNAi Sequences

| RNAi agent | Sequence | SEQ ID NO. | Luc-HCV Reporter Plasmid |
|---|---|---|---|
| 3'-7 | GCCGCATGACTGCAGAGAGT | SEQ ID NO. 49 | — |
| 3'-8 | ACTGGCCTCTCTGCAGATCA | SEQ ID NO. 50 | — |
| 3'-9 | TAGCCCTAGTCACGGCTAG | SEQ ID NO. 51 | — |
| 3'-10 | AGCTGTGAAAGGTCCGTGA | SEQ ID NO. 52 | — |
| 3'-11 | TAGCTGTGAAAGGTCCGTG | SEQ ID NO. 53 | — |
| 3'-12 | CTAGCTGTGAAAGGTCCGT | SEQ ID NO. 54 | — |
| 3'-13 | CTGTGAAAGGTCCGTGAGC | SEQ ID NO. 55 | — |
| 3'-14 | GAAAGGTCCGTGAGCCGCA | SEQ ID NO. 56 | — |

TABLE 2

Luciferase-HCV fusion reporter plasmids

| Reporter plasmid | Targets included |
|---|---|
| #20 | 5'1-through-5'5 |
| #16 | 5'3-through-5'10 |
| #17 | 5'6-through-5'10 |
| #12 | 5'7-through-5'10, Coding-1 |
| #18 | Coding-3 |
| #19 | 3'1-through-3'8 |
| C2&4 | Coding-2, Coding-4 |
| C5 | Coding-5 |
| C6 | Coding-6 |
| C7 | Coding-7 |
| C8 | Coding-8 |
| C9 | Coding-9 |
| C10 | Coding-10 |
| C11&12 | Coding-11, Coding-12 |
| C6-C9-C12-3'1 | Coding-6, Coding-9, Coding-12, 3'1 |

Example 1

Selection and Testing of 1-x RNAi Expression Cassettes Against Diseases or Disorders The selection of shRNAs useful as a therapeutic against diseases or disorders is not a straight-forward proposition. In addition to the problem of the generation of escape mutants in treating viral infections, the high mutation rate of both viral and cancerous genes leads to a rather large degree of sequence divergence within a population of affected individuals. For example, individuals infected with hepatitis virus may harbor virus with genotypes differing by as much as 31-34% in their nucleotide sequences, and subtypes (species within a given genotype) may differ by 20-23% based on full-length genomic sequence comparisons. Thus, in the case of HCV, regions of the viral genome with a high degree of conservation are identified and chosen to ensure the broadest therapeutic applicability. To select candidate sequences, an alignment of all published independent full-length or near-full-length sequences may be performed. When the sequence analyses are concluded, a list of candidate RNAi sequences is generated. In order to rank the sequences on the basis of relative potency, the ability of individual pre-synthesized RNAi agents to inhibit the activity of a target gene is tested. The same approach is used when targeting oncogenes, developmental genes and the like.

To test the efficacies of proposed RNAi agents, pre-synthesized RNAi agents are transfected into cells, tissues or organs of interest by standard techniques and reagents. An unrelated RNAi species is transfected into a parallel set of plates to serve as the negative control. Transfection efficiency is monitored by the inclusion of a small amount of non-specific RNAi into the transfection mixture that is end-labeled with fluorescein or phycoerythrin. The relative transfection efficiency is gauged by fluorescence microscopy prior to analysis of down regulation efficacy. At various time points post-transfection, the level of target gene activity is measured by one of a variety of methods.

Highly functional ddRNAi agents are selected and tested individually, and in the context of 1-x RNAi cassettes of the present invention. In embodiments where 1-x RNAi expression cassettes are used, RNAi agents are validated, and the coding sequences for each corresponding shRNA is generated from long, complementary self-annealing oligonucleotides and cloned into the individual sites in the 1-x RNAi cassette. This cassette is then inserted into a viral vector and this construct is then packaged into viral particles according to the methods described herein. Because the total length of each shRNAi component of the 1-x RNAi expression cassette is small (~70 nucleotides); linking up to five RNAi components together results in a sequence that is less than 350 nucleotides or so in length, and even including the promoter and terminator of the 1-x RNA expression cassette the total length is far below the upper size limit of for example, self-complementary AAV and other viral payload limits.

The inhibitory activity of the viral particles is tested on Huh-7 cells. Generation of a 1-x RNAi construct expressing unrelated shRNA species serves as a negative control. The efficacy of the shRNA sequences is monitored by aforementioned analysis techniques.

Example 2

Development of a 1-x RNAi Expression Construct

Construction of a 1-x RNAi expression construct includes a promoter driving the expression of the three or more individual shRNA species at comparable levels of abundance. The synthesis of small nuclear RNAs and transfer RNAs is directed by RNA polymerase III (pol III) under the control of pol III-specific promoters. Because of the relatively high abundance of transcripts directed by these regulatory elements, pol III promoters, including those derived from the U6 and H1 genes, have been used to drive the expression of 1-x RNAi (see, e.g., Domitrovich and Kunkel. *Nucl. Acids Res.* 31(9): 2344-52 (2003); Boden, et al. *Nucl. Acids Res.* 31(17): 5033-38 (2003a); and Kawasaki, et al. *Nucleic Acids Res.* 31(2): 700-7 (2003)).

Figure 4:
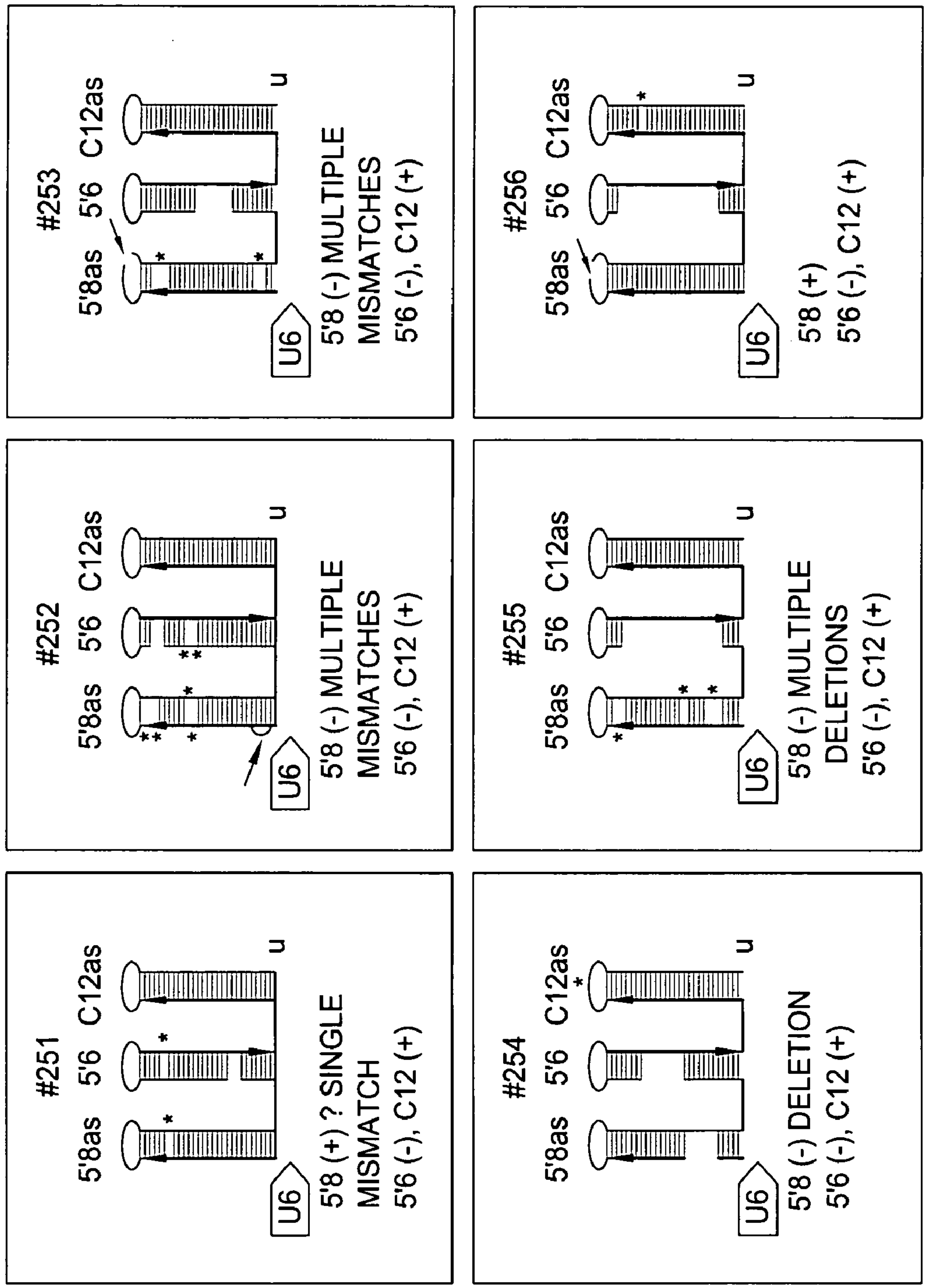
FIG. 4 shows a schematic diagram of 1-3 RNAi expression cassettes used in examples describe herein. A predictive outcome for siRNA activity is listed below each construct on the basis of pre-established art governing RNA interference mechanistic action.

Test 1-3 RNAi expression constructs (#251-#256) using the U6 promoter are shown in FIG. 4. They comprise three RNAi agents targeting three different regions of the HCV genome. The sequence in the cassettes is varied in order to test the various structural requirements needed for siRNA function. A predictive outcome is listed below each construct in FIG. 4 on the basis of pre-established art governing RNA interference mechanistic action. A predicted successful siRNA function outcome is shown as a "+" and a predicted unsuccessful siRNA function outcome is shown as a "–". In instances in which the predictive outcome results in a failure, the reason for the prediction is due to either deleted or mismatched sequences. Question marks indicate that the problem may or may not be significant enough to abrogate the activity of the hairpin construct.

Figure 7:
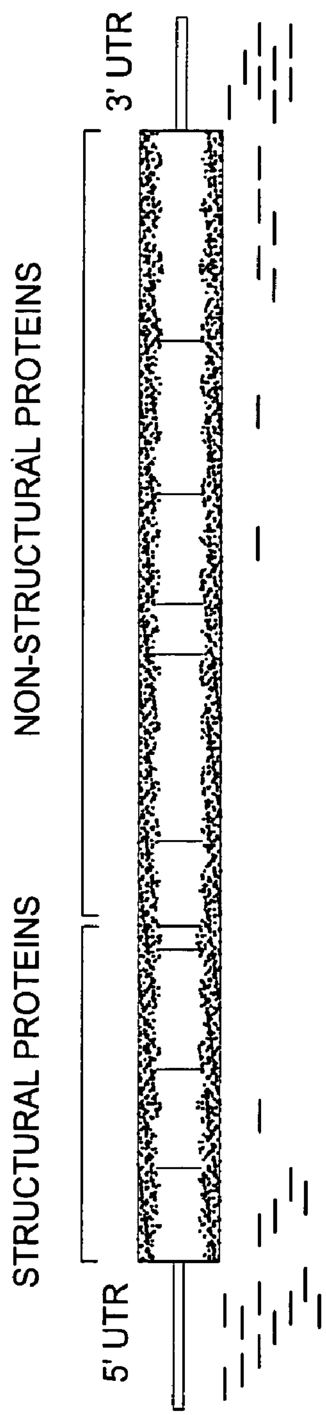
FIG. 7 shows a schematic diagram of the position of selected RNAi targets in HCV genome. Ten conserved targets were identified in the HCV IRES region, twelve in the ORF, and eight in the 3' untranslated region (3'UTR). Also shown is a schematic of the Luc-HCV fusion reporter construct used to assess 1-x RNAi inhibition.

To test the efficacy of the RNAi sequences selected, 1-x RNAi expression constructs of this invention were delivered directly to cultured cells along with a Luc-HCV reporter plasmid. The Luc-HCV plasmid used is the construct shown in FIG. 7, and comprises a luciferase sequence fused to various 100, 90, 80, 70, 60, 50, 40, 30 or 20 bp HCV target sequences (Note: for multiple targets within one reporter, 100 Bp is correct, while for most single target reporters this sequence corresponds to the target plus 5 nucleotides on the 5' and 3' ends)—the regions of HCV from which the RNAi sequences were derived. RNAi agents targeting a sequence segment within the 100 bp region will, if effective, degrade the HCV-luciferase transcription product, thus decreasing (perhaps eliminating) luciferase expression. Table 1 lists RNAi agents, some of which were tested. Table 2 lists some of the corresponding Luc-HCV reporter plasmids and the target HCV target regions used. FIG. 7 shows a schematic diagram of the position in the HCV genome of the targets of the RNAi agents of Table 1.

Figure 5:
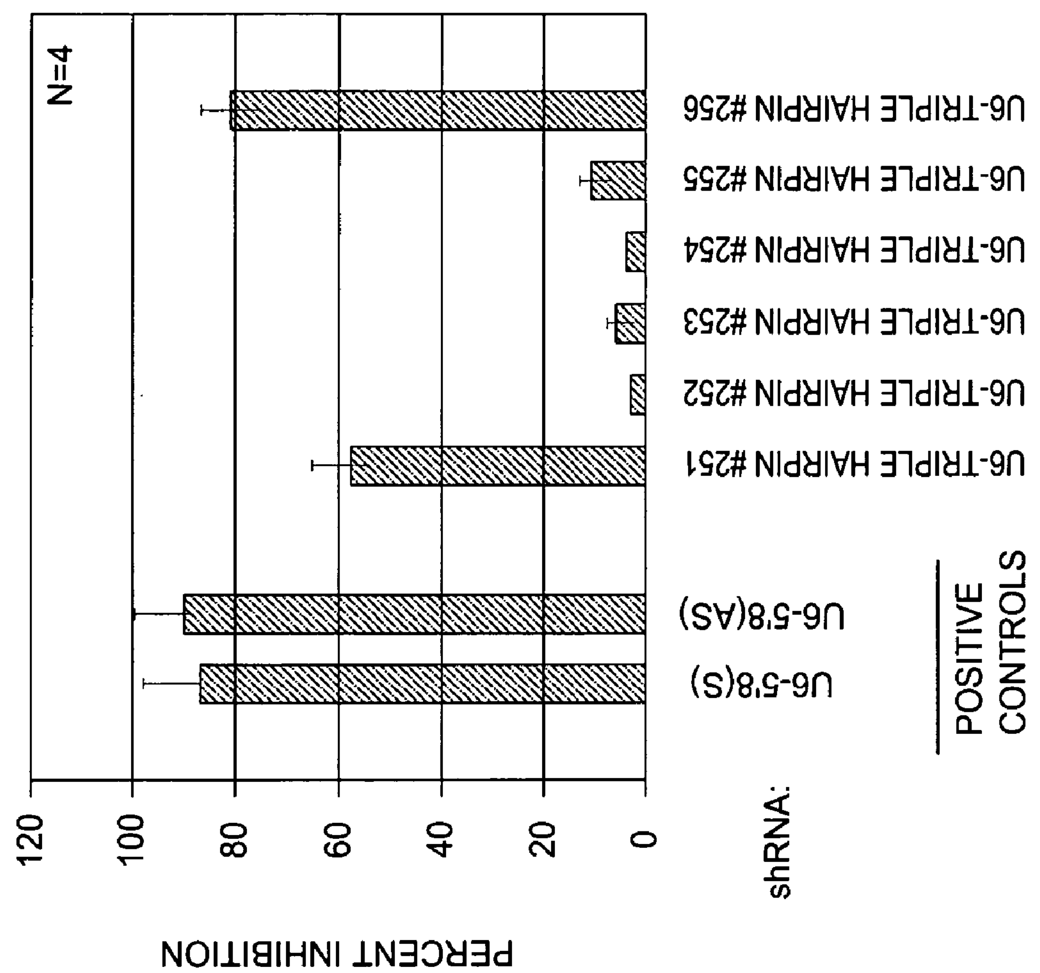
FIG. 5 shows the results of inhibition of a Luc-HCV fusion reporter construct containing the HCV 5'-8 target sequences by 1-3 RNAi expression cassette constructs of the present invention.
Figure 6:
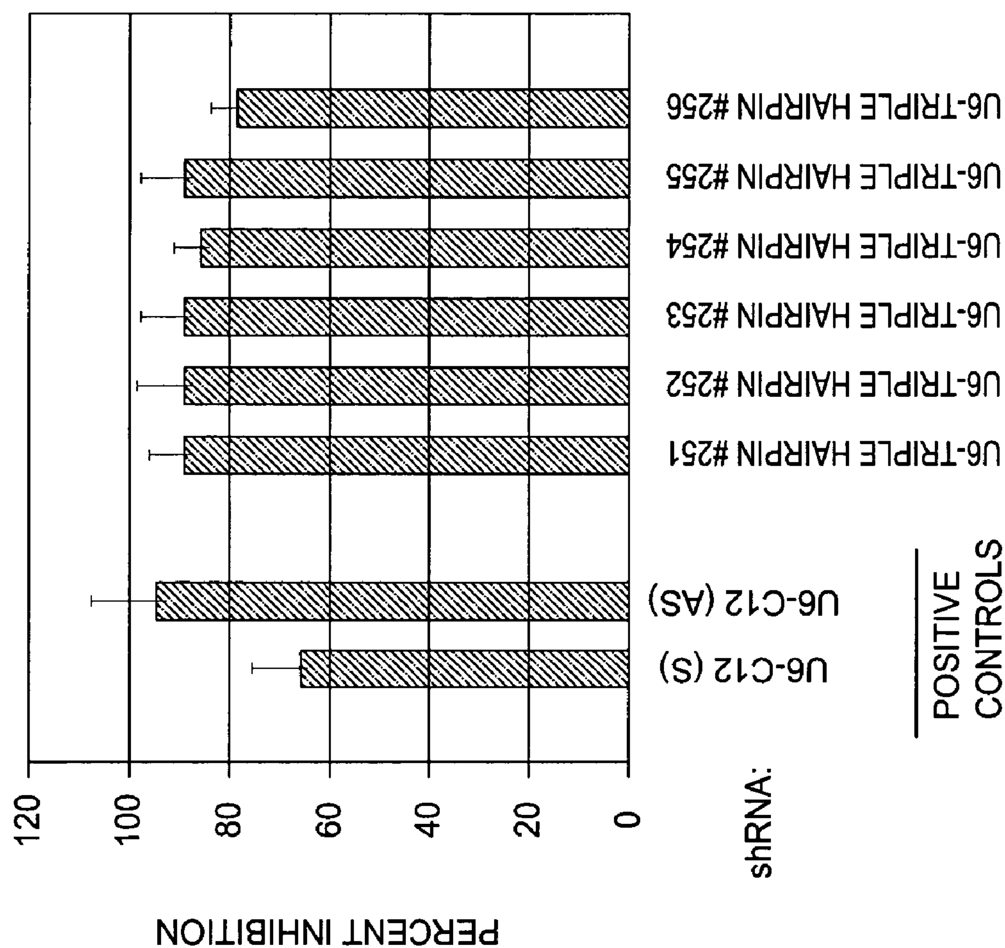
FIG. 6 shows the results of inhibition of a Luc-HCV fusion reporter construct containing the HCV coding-12 target sequences by 1-3 RNAi expression cassette constructs of the present invention.
Figure 8:
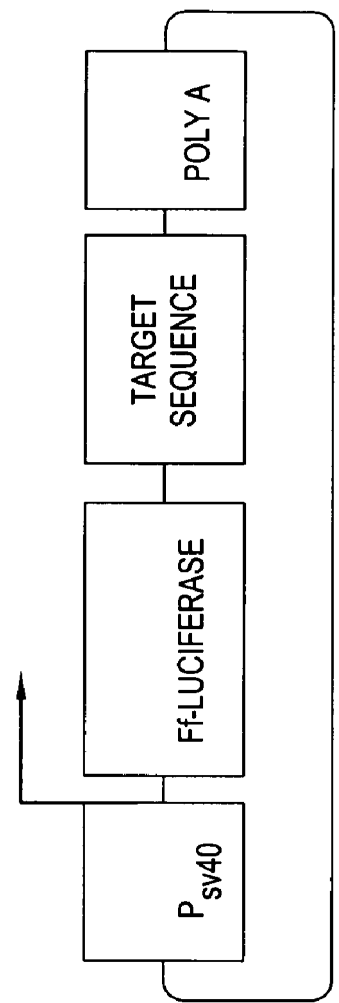
FIG. 8 shows a schematic of the Luc-HCV fusion reporter construct used to assess 1-x RNAi inhibition.

The relative strength of each 1-x RNAi construct was assessed in vitro by the decrease in activity of a co-transfected luciferase reporter, as seen in FIGS. 5 and 6. The test and reporter constructs were transfected into permissive cells utilizing standard techniques. The Luc-fusion reporter plasmid diagrammed in FIG. 8 was co-transfected into Huh-7 cells with an expression plasmid encoding for a triple hairpin shRNA species from FIG. 4. A plasmid for renilla luciferase expression was also included to normalize for transfection efficiency from sample to sample. A total of n=4 independent transfections were used for each condition. At 72 hours post-transfection, samples were harvested and assayed for relative levels of firefly luciferase activity. Plasmids containing the U6 promoter that drives the expression of a single shRNA against the 5'-8 or C-12 target sequences served as the positive controls for these experiments. A plasmid containing a U6 promoter, but no downstream shRNA sequence, served as the negative control and was thus utilized as the standard by which to assess levels of inhibition induced by the shRNA expression from the single and triple hairpin plasmids. 1-3 RNAi constructs containing RNAi targeting 5'8 a region in the 5'UTR of HCV, and the coding 12 region were co-transfected with luciferase HCV reporter plasmids containing the 5'8 or c12 target site. Luciferase expression was inhibited effectively only when the hairpins directed to the corresponding target site formed as predicted (i.e. with one or no mismatches in the predicted hairpin).

Example 3

In vivo Evaluation of the Triple Hairpin Constructs

In vivo evaluation of the triple hairpin constructs is evaluated by co-transfection of mouse liver with the appropriate luc-fusion reporter plasmid and 1-3 RNAi constructs 251, 252, 253, 254, 255, 256, a positive control plasmid, or a negative control plasmid using the hydrodynamic tail vein injection procedure. In addition, mice are injected with a plasmid expressing the human alpha one anti-trypsin ($\alpha$1-AT) protein that is used to normalize for transfection efficiency. Forty eight hours after injection, serum is collected from the animals, the animals are sacrificed, and the livers are harvested. Liver lysates are assayed for firefly luciferase activity using a Promega luciferase kit and serum samples are assayed for $\alpha$1-AT using an ELISA. Levels of inhibition induced by the 1-x RNAi expression from the hairpin constructs are assessed relative to the negative control.

Example 4

Figure 9:
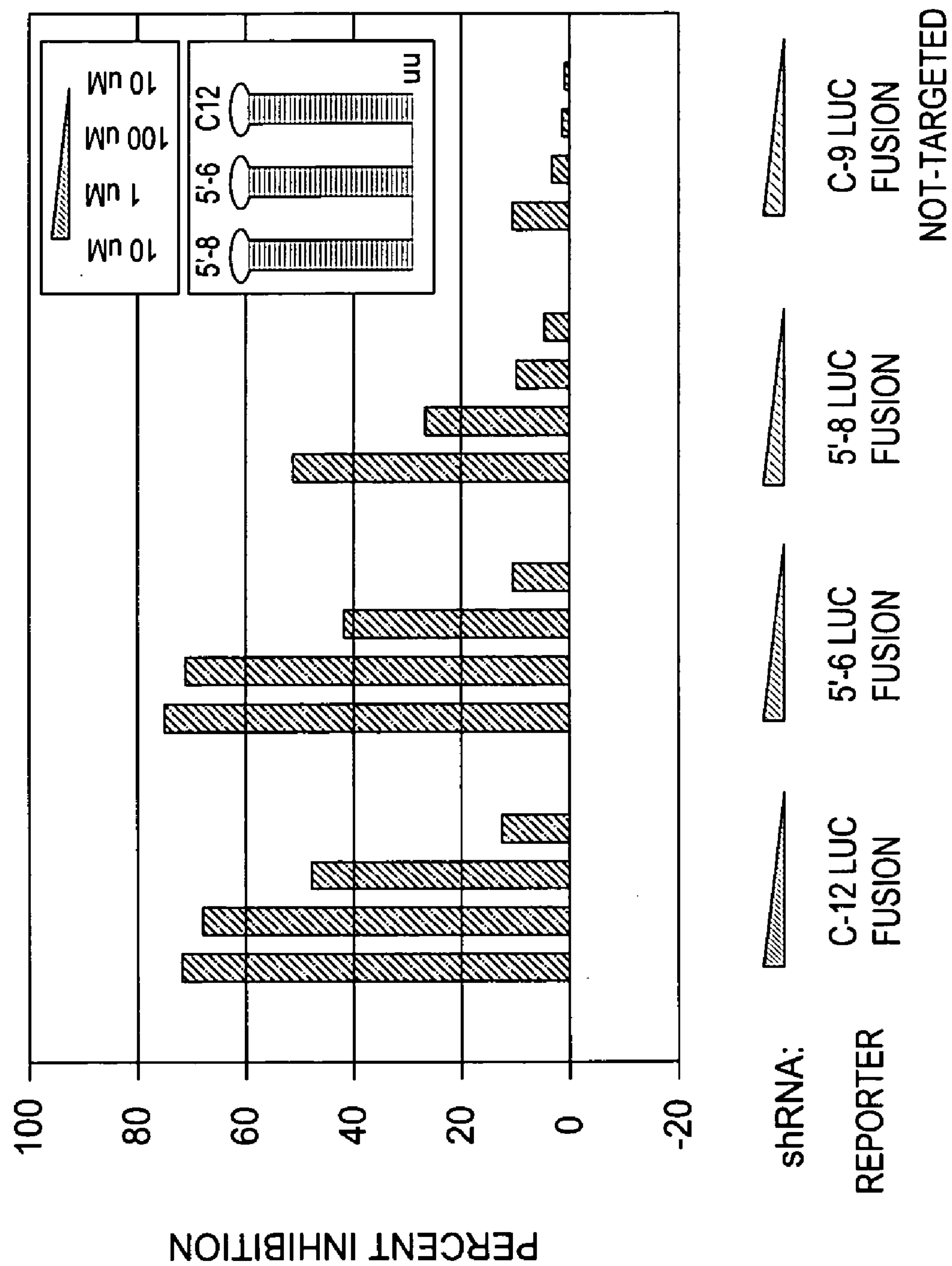
FIG. 9 shows the results of inhibiting a series of Luc-HCV fusion reporter constructs containing the target sequences by transfected RNA species produced in vitro. The RNA was generated from a run-off transcription reaction by T7 RNA Polymerase using a DNA template that contained the 1-3 RNAi expression cassette construct of the present invention.

The 1-x RNAi expression cassette may also be useful as a template for the production of RNAi species that can be administered directly to cells or tissues by utilizing one of the aforementioned nucleic acid delivery techniques. To show the utility of this type of approach, a T7 promoter was introduced upstream of the 1-x RNAi expression cassette containing three shRNA hairpins directed against independent reporter constructs containing either the 5'-8, 5'6 or C-12 target sequence of HCV. In order to use a run-off transcription technique to generate RNA containing the RNAi sequences in vitro, the template was prepared using a restriction enzyme digest that resulted in a cleavage of the plasmid just downstream of the 1-x RNAi expression cassette. T7 RNA polymerase was added into the reaction for the generation of RNA transcripts containing the 1-x expression cassette sequences. In the current example, the run-off transcripts were introduced into cells at various concentrations along with a set concentration of a series of the corresponding luciferase reporter constructs, using a lipophilic compounds as a transfection reagent. A separate DNA plasmid encoding for renilla luciferase protein expression was used to normalize for differences in transfection efficiencies between samples. A total of N=4 transfections were used for each condition and percent inhibition was calculated for each reporter construct with a set of samples that was transfected with a mixture only containing the appropriate reporter construct and renilla plasmids. The results, shown in FIG. 9, demonstrate a dose-dependent knockdown of all three reporter constructs by the in vitro transcribed 1-x expression construct. Non-specific inhibition was monitored by a non-targetable reporter construct (C9 luc fusion) and showed very little inhibition in response to the in vitro transcribed triple hairpin.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material or process to the objective, spirit and scope of the present invention. All such modifications are intended to be within the scope of the invention.

All references cited herein are to aid in the understanding of the invention, and are incorporated in their entireties for all purposes without limitation.

What is claimed is:

1. A 1-x RNAi expression cassette encoding x stem-loop structures, wherein x is two or more, and the stem-loop structures are separated from one another by one or more spacer regions, wherein the stem-loop structures are RNAi agents and at least one of the RNAi agents is encoded by SEQ ID NO:42.

2. The 1-x RNAi expression cassette of claim 1, wherein at least one of the RNAi agents is encoded by SEQ ID NO:6 or SEQ ID NO:39.

3. The 1-x RNAi expression cassette of claim 1, wherein x is 3, 4 or 5 stem loop structures.

4. The 1-x RNAi expression cassette of claim 3, wherein at least one of the RNAi agents is encoded by SEQ ID NO:6, and at least one of the RNAi agents is encoded by SEQ ID NO:39.

5. The 1-x RNAi expression cassette of claim 1, wherein the spacer regions are about 6 nucleotides.

6. The 1-x RNAi expression cassette of claim 1, wherein the stem of the stem-loop structures comprises about 19 base pairs.

7. The 1-x RNAi expression cassette of claim 1, wherein the loop of the stem-loop structures comprises about 5 to 9 nucleotides.

8. The 1-x RNAi expression cassette of claim 1, wherein the expression cassette further comprises a terminator sequence.

9. The 1-x RNAi expression cassette of claim 8, wherein the promoter and the terminator are from the same gene.

10. A method of modifying the expression of one or more genes, comprising:

introducing to a cell, tissue, or organ of interest a 1-x RNAi expression cassette encoding x stem-loop structures, wherein x is two or more and the stem-loop structures are separated from one another by one or more spacer regions, wherein the stem-loop structures are RNAi agents and at least one of the RNAi agents is encoded by SEQ ID NO:42.

11. The method of claim 10, wherein at least one of the RNAi agents is encoded by SEQ ID NO:6 or SEQ ID NO:39.

12. The method of claim 10, wherein introducing the 1-x RNAi expression cassette to a cell, tissue, or organ of interest comprises:

ligating the 1-x RNAi expression cassette into a viral delivery vector to form a viral RNAi expression construct;

packaging the viral RNAi expression construct into viral particles; and delivering the viral particles to the cell, tissue, or organ of interest.

13. The method of claim 10, wherein at least one of the RNAi agents is encoded by SEQ ID NO:6, and at least one of the RNAi agents is encoded by SEQ ID NO: 39.

14. The method of claim 10, wherein the stem of the stem-loop structures comprises about 19 base pairs.

15. The method of claim 10, wherein the loop of the stem-loop structures comprises about 5 to 9 nucleotides.

16. The method of claim 10, wherein the expression cassette further comprises a terminator sequence.

17. A method of modifying the expression of one or more genes, comprising:

introducing to a cell, tissue, or organ of interest an RNAi sequence that is an in vitro transcription product of a 1-x RNAi expression cassette wherein x is two or more and the stem-loop structures are separated from one another by one or more spacer regions, wherein the stem-loop structures are RNAi agents and at least one of the RNAi agents is encoded by SEQ ID NO: 42.

18. The method of claim 17, wherein the 1-x RNAi expression cassette further comprises a terminator sequence.

19. The method of claim 17, wherein the RNAi sequence comprises three stem-loop structures and the promoter is a T7 promoter.

* * * * *